United States Patent
Ameriks et al.

(10) Patent No.: US 10,100,045 B2
(45) Date of Patent: Oct. 16, 2018

(54) 3-ARYL-2H-PYRAZOLO[4,3-B]PYRIDINE COMPOUNDS AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Brian Ngo Laforteza, San Diego, CA (US); Brad M. Savall, San Diego, CA (US); Warren Stanfield Wade, San Diego, CA (US); Stephen Todd Meyer, San Diego, CA (US); Márió Gyuris, Budapest (HU)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/790,884

(22) Filed: Oct. 23, 2017

(65) Prior Publication Data

US 2018/0111925 A1    Apr. 26, 2018

Related U.S. Application Data

(60) Provisional application No. 62/412,870, filed on Oct. 26, 2016.

(51) Int. Cl.
| | | |
|---|---|---|
| C07D 401/14 | (2006.01) | |
| A61K 31/437 | (2006.01) | |
| C07D 417/14 | (2006.01) | |
| C07D 471/04 | (2006.01) | |

(52) U.S. Cl.
CPC ......... C07D 417/14 (2013.01); C07D 401/14 (2013.01); C07D 471/04 (2013.01)

(58) Field of Classification Search
CPC .......................... C07D 401/14; A61K 31/437
USPC ........................................ 514/303; 546/119
See application file for complete search history.

(56) References Cited

U.S. PATENT DOCUMENTS 6,613,777 B1 *    9/2003    Chen .................... C07D 471/04
                                                                     514/303

FOREIGN PATENT DOCUMENTS

| WO | WO 2000/001376 | 1/2000 |
|---|---|---|
| WO | WO 2011/100607 | 8/2011 |
| WO | WO 2015/183673 | 12/2015 |

OTHER PUBLICATIONS

Bagshawe, *Drug Dev Res.* 1995, 34, 220-230.
Bertolini, et al., *J Med Chem.* 1997, 40, 2011-2016.
Bodor, *Adv Drug Res.* 1984, 13, 224-331.
Brewer, G. J. (1997). "Isolation and culture of adult rat hippocampal neurons." Journal of Neuroscience Methods 71(2): 143-155.
Chen et al., *Bipolar Disord.*, 13:1-15, 2011.
Cho et al. (2007). "Two families of TARP isoforms that have distinct effects on the kinetic properties of AMPA receptors and synaptic currents." Neuron 55(6): 890-904.
Du et al., *J Neurosci* 24: 6578-6589, 2004.
Du et al., *J Neurosci* 28: 68-79, 2008.
Engin and Treit, *Behav Pharmacol* 18:365-374, 2007.
Fleisher et al., *Adv. Drug Delivery Rev.* 1996, 19, 115-130.
G.D. Considine, ed., Van Nostrand's Encyclopedia of Chemistry, p. 261, $5^{th}$ ed. (2005).
G.S. Paulekuhn, et al., "Trends in Active Pharmaceutical Ingredient Salt Selection based on Analysis of the Orange Book Database", *J. Med. Chem.*, 2007, 50:6665-72.
Gill and Bredt., *Neuropsychopharmacology* 36(1): 362-363 (2011).
Harrison, *Brain* 125:1428-1449, 2002.
Heckers and Konradi, *Curr Top Behav Neurosci.* 4:529-553, 2010.
Lazzaro et al. (2002). "Functional characterization of Cp-465,022, a selective, noncompetitive AMPA receptor antagonist." *Neuropharmacology* 42(2): 143-153.
McNaughton et al., *Behav Pharmacol* 18: 329-346, 2007.
Nolen and Bloemkolk, *Neuropsychobiology*, 42 Suppl 1:11-7, 2000.
Robinson et al., *J Med Chem.* 1996, 39 (1), 10-18.
Rogawski, Michael A., "Revisiting AMPA Receptors as an AntiEpileptic Drug Target" *Epilepsy Currents* 11.2 (2011).
S.M. Berge, et al., "Pharmaceutical Salts", *J Pharm Sci.*, 1977, 66:1-19.
Schobel et al., *Arch Gen Psych*, 66:938-946, 2009.
Shan, et al., *J Pharm Sci.* 1997, 86 (7), 765-767.
Shi et al (2009) "The stoichiometry of AMPA receptors and TARPs varies by neuronal cell type." *Neuron* 62(5): 633-640.

(Continued)

*Primary Examiner* — Niloofar Rahmani
(74) *Attorney, Agent, or Firm* — Thomas J. Dodd

(57) ABSTRACT

Provided herein are compounds of Formula (I), and pharmaceutically acceptable salts, N-oxides, or solvates thereof,

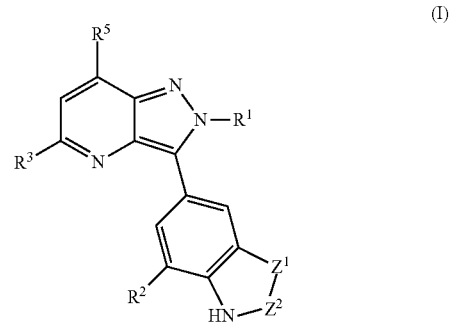

(I)

Also provided herein are pharmaceutical compositions comprising compounds of Formula (I) and methods of using compounds of Formula (I).

16 Claims, No Drawings

(56) References Cited

OTHER PUBLICATIONS

Small et al, *Nat. Rev. Neurosci.* 12:585-601, 2011.
Strange et al. (2006). "Functional characterisation of homomeric ionotropic glutamate receptors GluR1-GluR6 in a fluorescence-based high throughput screening assay." *Comb Chem High Throughput Screen* 9(2): 147-158.
Tomita et al. (2003). "Functional studies and distribution define a family of transmembrane AMPA receptor regulatory proteins." *J Cell Biol* 161(4): 805-816.
Tregellas et al., *Am J Psychiatry* 171: 549-556, 2014.
Yeung et al., *Hippocampus* 23:278-286, 2013.
Yeung et al., *Neuropharmacology* 62: 155-160, 2012.
International Search Report for PCT/US2017/057572 dated Jan. 12, 2018.

* cited by examiner

3-ARYL-2H-PYRAZOLO[4,3-B]PYRIDINE COMPOUNDS AND THEIR USE AS AMPA RECEPTOR MODULATORS

CROSS-REFERENCED TO RELATED APPLICATIONS

This application claims priority from U.S. Application No. 62/412,870, filed on Oct. 26, 2016, which is incorporated herein by reference.

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., *Neuropsychopharmacology* 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anticonvulsant activity are close to or overlap with doses at which undesired effects are observed. (Michael A. Rogawski. "Revisiting AMPA Receptors as an AntiEpileptic Drug Target" Epilepsy *Currents* 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, *Nat. Rev. Neurosci.* 12:585-601, 2011). A meta-analysis of post-mortem neuro-pathology studies suggests that hippocampal volume is reduced in volume in patients with mood disorders (Harrison, *Brain* 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., *Bipolar Disord.*, 13:1-15, 2011). Chronic treatment with mood stabilizers such as lithium or valproate reduced AMPA receptor surface expression in hippocampus (Du et al., *J Neurosci* 28: 68-79, 2008). Tricyclic antidepressants can trigger mania in bipolar patients (Nolen and Bloemkolk, *Neuropsychobiology*, 42 Suppl 1:11-7, 2000); these treatments can increase AMPA receptor surface expression in hippocampus (Du et al., *J Neurosci* 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of $GABA_A$ agonists is sufficient to replicate their anxiolytic effects (Engin and Treit, *Behav Pharmacol* 18:365-374, 2007). Traditional anxiolytics with a variety of mechanisms-of-action, including $GABA_A$-receptor antagonists, 5-HT1A receptor antagonists, and SSRIs, suppress brainstem-stimulated theta rhythm within hippocampus (McNaughton et al., *Behav Pharmacol* 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., *Hippocampus* 23:278-286, 2013). Intrahippocampal administration of phenytoin, a voltage-gated sodium channel inhibitor and anticonvulsant, showed similar effects on brainstem-stimulated theta rhythm frequency in anesthetized rat and was anxiolytic in conscious rat (Yeung et al., *Neuropharmacology* 62: 155-160, 2012).

Hippocampal overactivity has been observed in patients suffering from schizophrenia (Heckers and Konradi, *Curr Top Behav Neurosci.* 4:529-553, 2010). The degree of hyperactivity was be positively correlated to the severity of the symptoms (Tregellas et al., *Am J Psychiatry* 171: 549-556, 2014). Hypermetabolism in hippocampus (esp. CA1 region) correlates with disease progression in at-risk individuals, and with disease severity in patients diagnosed with schizophrenia (Schobel et al., *Arch Gen Psych,* 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, *Curr Top Behav Neurosci,* 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

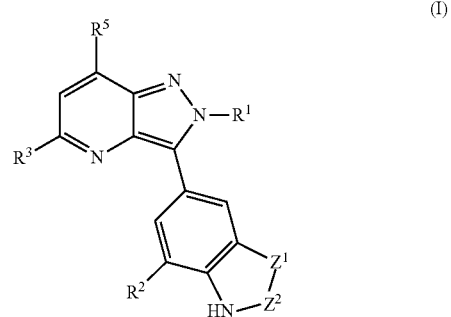

wherein
$R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl;
$R^2$ is selected from the group consisting of: H, halo, and $CH_3$;

$R^3$ is $C_{1-6}$haloalkyl;

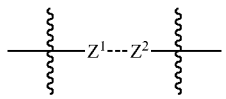

is selected from the group consisting of: —CH=N—, —CH$_2$—C(=O)—, —S—C(=O)—, and —NH—C(=O)—; and $R^5$ is H or CHF$_2$; and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or SPECT studies.

Additional embodiments of this invention include methods of making compounds of Formula (I) and Formula (IA), pharmaceutically acceptable salts, N-oxides or solvates of compounds of Formula (I) and Formula (IA), pharmaceutically acceptable prodrugs of compounds of Formula (I) and Formula (IA), and pharmaceutically active metabolites of Formula (I) and Formula (IA).

In a further aspect, provided herein are pharmaceutical compositions, comprising an effective amount of a compound of Formula (IA), as well as pharmaceutically acceptable salts, N-oxides or solvates of Formula (IA), pharmaceutically acceptable prodrugs of compounds of Formula (IA), and pharmaceutically active metabolites of Formula (IA).

In a further aspect, provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA), for the treatment of any condition described herein.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

In one aspect, provided herein are compounds of Formula (I),

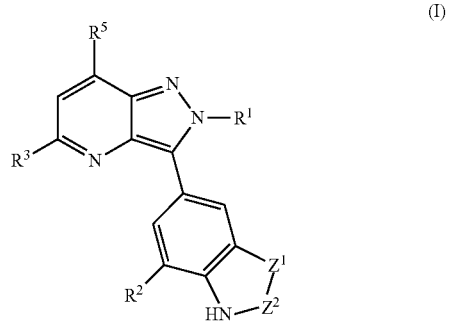

wherein $R^1$ is selected from the group consisting of: $C_{1-6}$alkyl, $C_{1-6}$haloalkyl, CH$_2$CH$_2$OCH$_3$, $C_{3-8}$cycloalkyl, CH$_2$—$C_{3-8}$cycloalkyl, phenyl and pyridyl;

$R^2$ is selected from the group consisting of: H, halo, and CH$_3$;

$R^3$ is $C_{1-6}$haloalkyl;

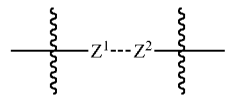

is selected from the group consisting of: —CH=N—, —CH$_2$—C(=O)—, —S—C(=O)—, and —NH—C(=O)—; and $R^5$ is H or $CHF_2$; and pharmaceutically acceptable salts, N-oxides, or solvates thereof.

An additional embodiment of the invention is a compound of Formula (I) wherein $R^1$ is $C_{1-6}$alkyl, $C_{1-6}$haloalkyl, $CH_2CH_2OCH_3$, $CH_2$cyclobutyl, cyclobutyl, cyclopentyl, phenyl, or pyridin-2-yl.

An additional embodiment of the invention is a compound of Formula (I) wherein $R^2$ is H, Cl or $CH_3$.

An additional embodiment of the invention is a compound of Formula (I) wherein $R^3$ is $CF_3$.

An additional embodiment of the invention is a compound of Formula (I) wherein $R^3$ is $CF_2H$.

An additional embodiment of the invention is a compound of Formula (I) wherein $$-Z^1---Z^2-$$

is —CH=N—.

An additional embodiment of the invention is a compound of Formula (I) wherein $$-Z^1---Z^2-$$

is —$CH_2$—C(=O)—.

An additional embodiment of the invention is a compound of Formula (I) wherein $$-Z^1---Z^2-$$

is —NH—C(=O)—.

An additional embodiment of the invention is a compound of Formula (I) wherein $$-Z^1---Z^2-$$

is —S—C(=O)—.

An additional embodiment of the invention is a compound of Formula (I) wherein $R^5$ is H.

An additional embodiment of the invention is a compound of Formula (I) wherein $R^5$ is $CHF_2$.

An additional embodiment of the invention is a compound of Formula (I) having the Formula (IA):

(IA)

wherein $R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl; and $R^4$ is selected from the group consisting of:

An additional embodiment of the invention is a compound of Formula (I) having the Formula (IA) wherein $R^4$ is An additional embodiment of the invention is a compound of Formula (I) having the Formula (IA) wherein $R^4$ is

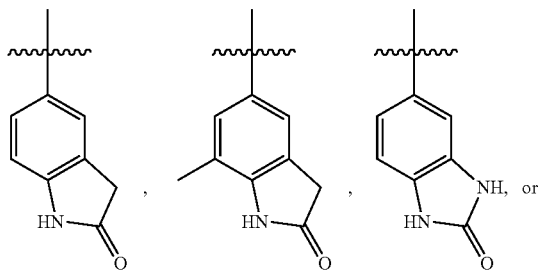, 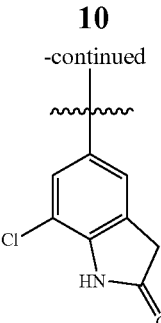

An additional embodiment of the invention is a compound selected from the group consisting of compounds of Formula (I), or Formula (IA), or a combination thereof.

A further embodiment of the current invention is a compound as shown below in Table 1.

| Ex # | Compound Name |
|---|---|
| 1 | 5-(2-Methyl-5-(trifluoromethyl)-2H-pyrazolo[4,3-b]pyridin-3-yl)-1,3-dihydro-2H-benzo[d]imidazol-2-one; |
| 2 | 7-Methyl-5-(2-methyl-5-(trifluoromethyl)-2H-pyrazolo[4,3-b]pyridin-3-yl)indolin-2-one; |
| 3 | 5-[2-(Difluoromethyl)-5-(trifluoromethyl)pyrazolo[4,3-b]pyridin-3-yl]-7-methyl-indolin-2-one; |
| 4 | 5-(2-Ethyl-5-(trifluoromethyl)-2H-pyrazolo[4,3-b]pyridin-3-yl)-1,3-dihydro-2H-benzo[d]imidazol-2-one; |
| 5 | 5-(2-Isopropyl-5-(trifluoromethyl)-2H-pyrazolo[4,3-b]pyridin-3-yl)-1,3-dihydro-2H-benzo[d]imidazol-2-one; |
| 6 | 5-(2-(Cyclobutylmethyl)-5-(trifluoromethyl)-2H-pyrazolo[4,3-b]pyridin-3-yl)-1,3-dihydro-2H-benzo[d]imidazol-2-one; |
| 7 | 5-(2-Cyclopentyl-5-(trifluoromethyl)-2H-pyrazolo[4,3-b]pyridin-3-yl)-1,3-dihydro-2H-benzo[d]imidazol-2-one; |
| 8 | 2-Cyclopentyl-3-(7-methyl-1H-indazol-5-yl)-5-(trifluoromethyl)-2H-pyrazolo[4,3-b]pyridine; |
| 9 | 5-(2-Phenyl-5-(trifluoromethyl)-2H-pyrazolo[4,3-b]pyridin-3-yl)-1,3-dihydro-2H-benzo[d]imidazol-2-one; |
| 10 | 5-(2-Phenyl-5-(trifluoromethyl)-2H-pyrazolo[4,3-b]pyridin-3-yl)indolin-2-one; |
| 11 | 3-(1H-Indazol-5-yl)-2-phenyl-5-(trifluoromethyl)-2H-pyrazolo[4,3-b]pyridine; |
| 12 | 2-Cyclobutyl-3-(1H-indazol-5-yl)-5-(trifluoromethyl)-2H-pyrazolo[4,3-b]pyridine; |
| 13 | 3-(1H-Indazol-5-yl)-2-(2-methoxyethyl)-5-(trifluoromethyl)-2H-pyrazolo[4,3-b]pyridine; |
| 14 | 3-(1H-Indazol-5-yl)-2-(pyridin-2-yl)-5-(trifluoromethyl)-2H-pyrazolo[4,3-b]pyridine; |
| 15 | 2-Methyl-3-(7-methyl-1H-indazol-5-yl)-5-(trifluoromethyl)-2H-pyrazolo[4,3-b]pyridine; |
| 16 | 3-(7-Chloro-1H-indazol-5-yl)-2-methyl-5-(trifluoromethyl)-2H-pyrazolo[4,3-b]pyridine; |
| 17 | 5-(2-Ethyl-5-(trifluoromethyl)-2H-pyrazolo[4,3-b]pyridin-3-yl)-7-methylindolin-2-one; |
| 18 | 7-Chloro-5-(2-ethyl-5-(trifluoromethyl)-2H-pyrazolo[4,3-b]pyridin-3-yl)indolin-2-one; |
| 19 | 2-Ethyl-3-(7-methyl-1H-indazol-5-yl)-5-(trifluoromethyl)-2H-pyrazolo[4,3-b]pyridine; |
| 20 | 3-(7-Chloro-1H-indazol-5-yl)-2-ethyl-5-(trifluoromethyl)-2H-pyrazolo[4,3-b]pyridine; |
| 21 | 5-(2-Isopropyl-5-(trifluoromethyl)-2H-pyrazolo[4,3-b]pyridin-3-yl)-7-methylindolin-2-one; |
| 22 | 7-Chloro-5-(2-isopropyl-5-(trifluoromethyl)-2H-pyrazolo[4,3-b]pyridin-3-yl)indolin-2-one; |
| 23 | 2-Isopropyl-3-(7-methyl-1H-indazol-5-yl)-5-(trifluoromethyl)-2H-pyrazolo[4,3-b]pyridine; |
| 24 | 3-(7-Chloro-1H-indazol-5-yl)-2-isopropyl-5-(trifluoromethyl)-2H-pyrazolo[4,3-b]pyridine; |
| 25 | 5-(2-Cyclobutyl-5-(trifluoromethyl)-2H-pyrazolo[4,3-b]pyridin-3-yl)-7-methylindolin-2-one; |
| 26 | 7-Chloro-5-(2-cyclobutyl-5-(trifluoromethyl)-2H-pyrazolo[4,3-b]pyridin-3-yl)indolin-2-one; |

-continued

| Ex # | Compound Name |
|---|---|
| 27 | 2-Cyclobutyl-3-(7-methyl-1H-indazol-5-yl)-5-(trifluoromethyl)-2H-pyrazolo[4,3-b]pyridine; |
| 28 | 3-(7-Chloro-1H-indazol-5-yl)-2-cyclobutyl-5-(trifluoromethyl)-2H-pyrazolo[4,3-b]pyridine; |
| 29 | 7-Chloro-5-(2-(difluoromethyl)-5-(trifluoromethyl)-2H-pyrazolo[4,3-b]pyridin-3-yl)indolin-2-one; |
| 30 | 2-(Difluoromethyl)-3-(7-methyl-1H-indazol-5-yl)-5-(trifluoromethyl)-2H-pyrazolo[4,3-b]pyridine; |
| 31 | 3-(7-Chloro-1H-indazol-5-yl)-2-(difluoromethyl)-5-(trifluoromethyl)-2H-pyrazolo[4,3-b]pyridine; |
| 34 | 5-(Difluoromethyl)-2-isopropyl-3-(7-methyl-1H-indazol-5-yl)-2H-pyrazolo[4,3-b]pyridine; |
| 36 | 7-Chloro-5-(5-(difluoromethyl)-2-isopropyl-2H-pyrazolo[4,3-b]pyridin-3-yl)indolin-2-one; |
| 38 | 7-(Difluoromethyl)-2-isopropyl-3-(7-methyl-1H-indazol-5-yl)pyrazolo[4,3-b]pyridine; |
| 39 | 3-(7-Chloro-1H-indazol-5-yl)-2-isopropyl-pyrazolo[4,3-b]pyridine; and |
| 40 | 5,7-Bis(difluoromethyl)-2-isopropyl-3-(7-methyl-1H-indazol-5-yl)pyrazolo[4,3-b]pyridine; and | pharmaceutically acceptable salts, N-oxide, or solvates thereof.

A further embodiment of the current invention is a compound selected from the group consisting of:
6-(2-Isopropyl-5-(trifluoromethyl)-2H-pyrazolo[4,3-b]pyridin-3-yl)benzo[d]thiazol-2(3H)-one;
3-(7-Chloro-1H-indazol-5-yl)-5-(difluoromethyl)-2-isopropyl-2H-pyrazolo[4,3-b]pyridine;
5-(5-(Difluoromethyl)-2-isopropyl-2H-pyrazolo[4,3-b]pyridin-3-yl)-7-methylindolin-2-one; and
6-(5-(Difluoromethyl)-2-isopropyl-2H-pyrazolo[4,3-b]pyridin-3-yl)benzo[d]thiazol-2(3H)-one; and
pharmaceutically acceptable salts, N-oxides or solvates thereof.

An additional embodiment of the invention is a pharmaceutical composition comprising:

(A) an effective amount of at least one compound of Formula (I):

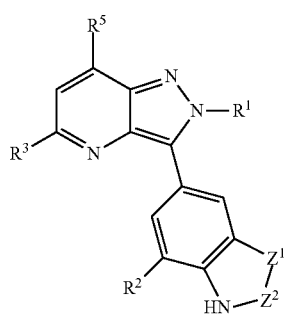

(I)

wherein
$R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl;
$R^2$ is selected from the group consisting of: H, halo, and $CH_3$;
$R^3$ is $C_{1-6}$haloalkyl;

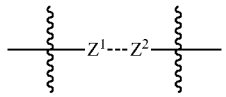

is selected from the group consisting of: —CH=N—, —CH$_2$—C(=O)—, —S—C(=O)—, and —NH—C(=O)—; and
$R^5$ is H or $CHF_2$; and
pharmaceutically acceptable salts, N-oxides or solvates of compounds of Formula (I); and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

Also within the scope of the invention are enantiomers and diastereomers of the compounds of Formula (I). Also within the scope of the invention are the pharmaceutically acceptable salts, N-oxides or solvates of the compounds of Formula (I). Also within the scope of the invention are the pharmaceutically acceptable prodrugs of compounds of Formula (I), and pharmaceutically active metabolites of the compounds of Formula (I).

Also within the scope of the invention are isotopic variations of compounds of Formula (I) (as well as Formula (IA)), such as, e.g., deuterated compounds of Formula (I) (as well as Formula (IA)). Also within the scope of the invention are the pharmaceutically acceptable salts, N-oxides or solvates of the isotopic variations of the compounds of Formula (I) (as well as Formula (IA)). Also within the scope of the invention are the pharmaceutically acceptable prodrugs of the isotopic variations of the compounds of Formula (I) (as well as Formula (IA)), and pharmaceutically active metabolites of the isotopic variations of the compounds of Formula (I) (as well as Formula (IA)).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

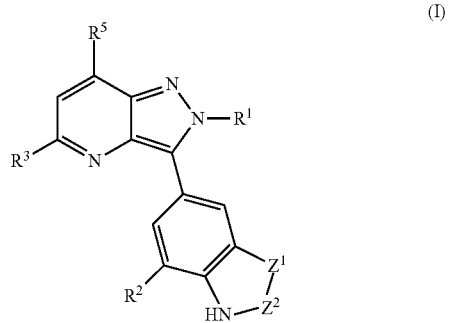

wherein
$R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl;
$R^2$ is selected from the group consisting of: H, halo, and $CH_3$;
$R^3$ is $C_{1-6}$haloalkyl;

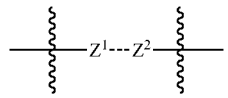

is selected from the group consisting of: —CH=N—, —$CH_2$—C(=O)—, —S—C(=O)—, and —NH—C(=O)—; and
$R^5$ is H or $CHF_2$; and
pharmaceutically acceptable salts, N-oxides, or solvates thereof, to a subject in need thereof.

In a further aspect, provided herein is a method of treating a subject suffering from or diagnosed with a disease, disorder, or medical condition mediated by AMPA receptor activity, comprising administering to a subject in need of such treatment an effective amount of at least one compound selected from compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA).

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxia, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxia, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes.

The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_1$-$C_6$alkyl group. In some embodiments, an alkyl group is a $C_1$-$C_4$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$haloalkyl group. In some embodiments, a haloalkyl group is a $C_1$-$C_4$haloalkyl group. One exemplary substitutent is fluoro. Preferred substituted alkyl groups of the invention include trihalogenated alkyl groups such as trifluoromethyl groups.

Haloalkyl includes and is not limited to $CF_3$, $CH_2F$, $CHF_2$, $CH_2Cl$, $CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

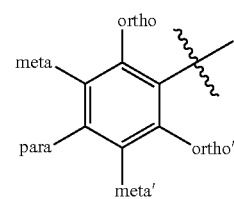

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

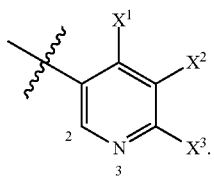

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding MgSO$_4$ and NaHCO$_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Compounds of the invention may also exist as "rotamers," that is, conformational isomers that occur when the rotation leading to different conformations is hindered, resulting a rotational energy barrier to be overcome to convert from one conformational isomer to another.

A wavy line "〜" indicates the point of attachment to the rest of the molecule.

Additionally, any formula given herein is intended to refer also to hydrates, solvates, and polymorphs of such compounds, and mixtures thereof, even if such forms are not listed explicitly.

Certain compounds of Formula (I) (as well as Formula (IA)), or pharmaceutically acceptable salts of of Formula (I) (as well as Formula (IA)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formula (IA)) or pharmaceutically acceptable salts of compounds of Formula (I) (as well as Formula (IA)) may be obtained as co-crystals. In certain embodiments of the invention, compounds of Formula (I) (as well as Formula (IA)) were obtained in a crystalline form. In other embodiments, crystalline forms of compounds of Formula (I) (as well as Formula (IA)) were cubic in nature. In other embodiments, pharmaceutically acceptable salts of compounds of Formula (I) (as well as Formula (IA)) were obtained in a crystalline form. In still other embodiments, compounds of Formula (I) (as well as Formula (IA)) were obtained in one of several polymorphic forms, as a mixture of crystalline forms, as a polymorphic form, or as an amorphous form. In other embodiments, compounds of Formula (I) (as well as Formula (IA)) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R-COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R-COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium or tritium (i.e., $^2$H, $^3$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent S$^1$$_{example}$ is one of S$_1$ and S$_2$, and substituent S$^2$$_{example}$ is one of S$_3$ and S$_4$, then these assignments refer to embodiments of this invention given according to the choices S$^1$$_{example}$ is S$_1$ and S$^2$$_{example}$ is S$_3$; S$^1$$_{example}$ is S$_1$ and S$^2$$_{example}$ is S$_4$; S$^1$$_{example}$ is S$_2$ and S$^2$$_{example}$ is S$_3$; S$^1$$_{example}$ is S$_2$ and S$^2$$_{example}$ is S$_4$; and equivalents of each one of such choices. The shorter terminology "S$^1$$_{example}$ is one of S$_1$ and S$_2$, and S$^2$$_{example}$ is one of S$_3$ and S$_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, HAL, $Z^1$, $Z^2$, and $Z^3$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such $R^1$, $R^2$, $R^3$, $R^4$, $R^5$, HAL, $Z^1$, $Z^2$, and $Z^3$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formula (IA)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formula (IA)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formula (IA)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formula (IA)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formula (IA)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I), and Formula (IA) as well, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formula (IA)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formula (IA)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formula (IA)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formula (IA)), which may also be used in the methods of the invention. A "pharmaceutically active metabolite" means a pharmacologically active product of metabolism in the body of a compound of Formula (I) (as well as Formula (IA)) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formula (IA)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I), as well as Formula (IA), as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease.

The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), as well as Formula (IA). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Table 2. Abbreviations and acronyms used herein include the following.

TABLE 2

| Term | Acronym/Abbreviation |
| --- | --- |
| Chloroform | $CHCl_3$ |
| cesium carbonate | $Cs_2C_2O_3$ |
| cesium fluoride | CsF |
| copper (II) sulfate | $Cu_2SO_4$ |
| Dichloromethane | DCM |
| N,N-dimethylformamide | DMF |
| Dimethylsulfoxide | DMSO |
| ethyl acetate | EtOAc |
| Ethanol | EtOH |
| hydrochloric acid | HCl |
| High-Pressure Liquid Chromatography | HPLC |
| potassium carbonate | $K_2CO_3$ |
| potassium acetate | KOAc |
| magnesium sulfate | $MgSO_4$ |
| sodium fluoride | NaF |
| sodium hydroxide | NaOH |
| sodium sulfate | $Na_2SO_4$ |
| Ammonia | $NH_3$ |
| nitrogen gas | $N_2$ |
| [1,1'-bis(diphenylphosphino)ferrocene]dichloropalladium(II) | $Pd(dppf)Cl_2$ |
| tetrakis(triphenylphosphine) palladium(0) | $Pd(PPh_3)_4$ |
| room temperature | rt |
| tert-butyl hydroperoxide | TBHP |
| trifluoroacetic acid | TFA |
| Tetrahydrofuran | THF |
| para-toluene sulfonate | para-toluene sulfonate |

PREPARATIVE EXAMPLES

Exemplary compounds useful in methods of the invention will now be described by reference to the illustrative synthetic schemes for their general preparation below and the specific examples to follow.

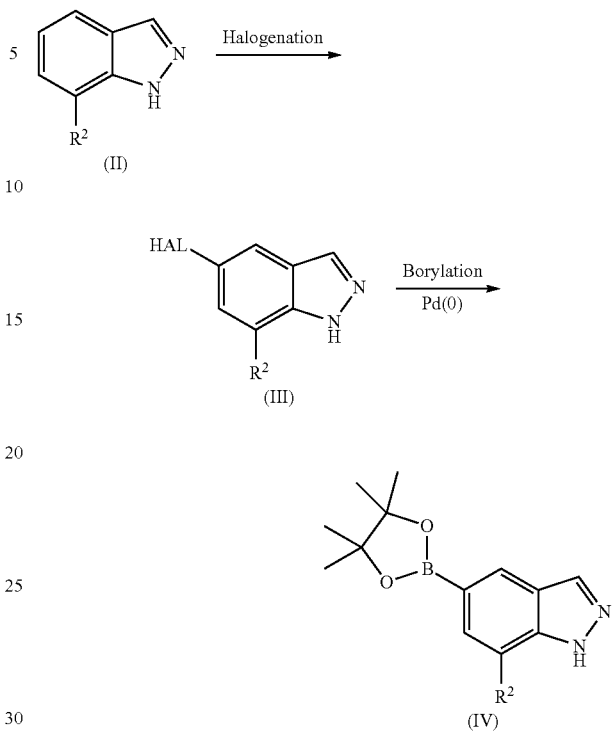

According to SCHEME 1, a compound of formula (IV), where $R^2$ is hydrogen, halogen, or $CH_3$, is commercially available or synthetically accessible from a compound of formula (II), where $R^1$ is defined as above. An indazole compound of formula (II) is treated with an electrophilic halogen source such as bromine, in a suitable solvent such as TFA, to provide a compound of formula (III). A compound of formula (III) is treated with a borylating agent such as bis(pinacolato)diboron, in the presence of a palladium catalyst such as $Pd(dppf)Cl_2$, and a suitable base, such as potassium acetate, employing conventional heating, at a temperature such as 100° C., in a solvent such as 1,4-dioxane, and the like, to provide a compound of formula (IV), where $R^2$ is hydrogen, halogen, or $CH_3$.

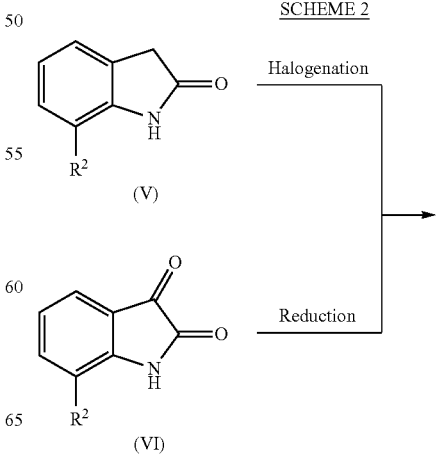

-continued

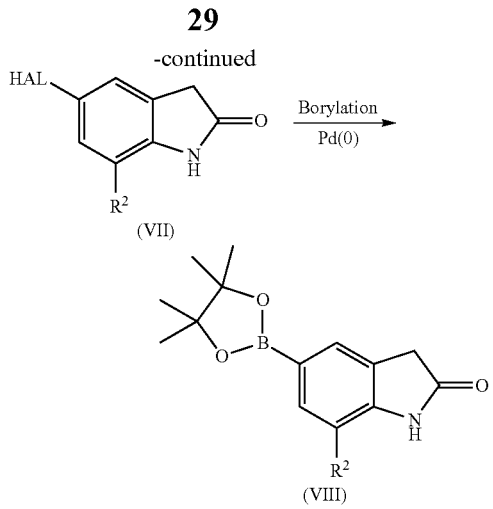

According to SCHEME 2, a compound of formula (VIII), where $R^2$ is a hydrogen, halogen, or $CH_3$, is commercially available or synthetically accessible from a compound of formula (V) or formula (VI), where $R^2$ is defined as above. An indolone compound of formula (V) is treated with an electrophilic halogen source such as bromine, in a suitable solvent such as TFA, to provide a compound of formula (VII). Alternatively, an isatin compound of formula (VI) is treated with a reducing agent such as zinc, in the presence of a Lewis Acid such as titanium tetracholoride, and the like, in a suitable solvent such as THF, and the like, to provide a compound of formula (VII). A compound of formula (VII) is treated with a borylating agent such as bis(pinacolato) diboron, in the presence of a palladium catalyst such as Pd(dppf)Cl$_2$, and the like, and a suitable base, such as potassium acetate, employing conventional heating, at a temperature such as 100° C., in a solvent such as 1,4-dioxane, and the like, to provide a compound of formula (VIII), where $R^2$ is defined as above.

SCHEME 3

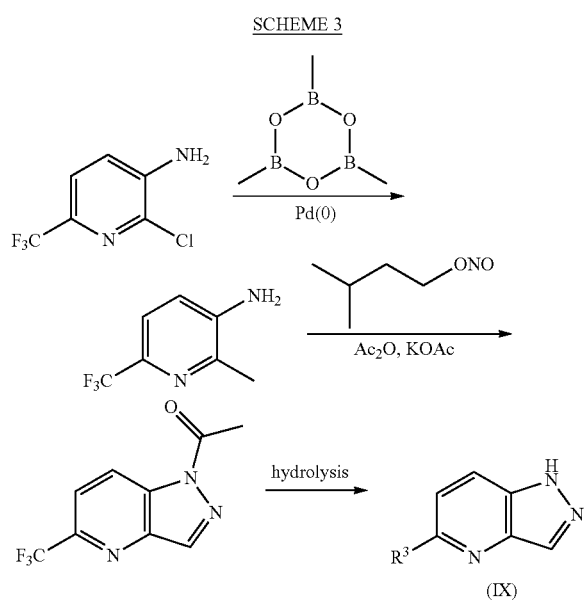

According to SCHEME 3, 2-chloro-6-(trifluoromethyl) pyridin-3-amine is treated with a methylating agent such as trimethylboroxine, in the presence of a catalyst such as Pd(dppf)Cl$_2$, and the like, a suitable base such as $K_2CO_3$, and the like, employing conventional heating, at a temperature such as 110° C., in a solvent such as 1,4-dioxane, and the like, to provide 2-methyl-6-(trifluoromethyl)pyridine-3-amine. 2-Methyl-6-(trifluoromethyl)pyridine-3-amine is treated with an aminating reagent such as isopentylnitrite, in the presence of acetic anhydride, potassium acetate, and 18-Crown-6, in a suitable solvent such as CHCl$_3$, employing conventional heating, at a temperature such as 100° C., to provide 1-(5-(trifluoromethyl)-1H-pyrazolo[4,3-b]pyridin-1-yl)ethanone. 1-(5-(Trifluoromethyl)-1H-pyrazolo[4,3-b]pyridin-1-yl)ethanone is treated with a base such as potassium carbonate, in a suitable solvent system such as methanol and water, to provide a compound of formula (IX), where $R^3$ is CF$_3$.

SCHEME 4

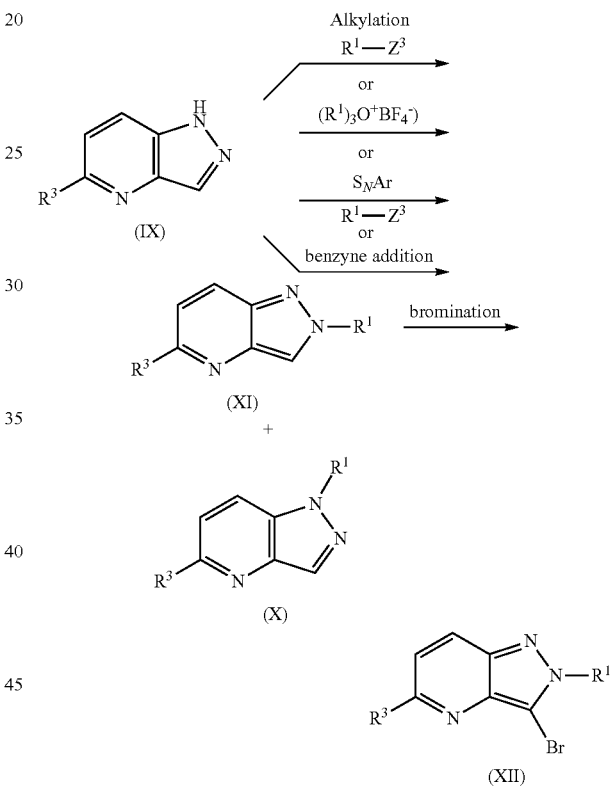

According to SCHEME 4, a compound of formula (IX), where $R^3$ is CF$_3$, is treated with an alkylating reagent of formula $R^1$—$Z^3$, where $R^1$ is $C_{1-5}$alkyl, CH$_2$CH$_2$OCH$_3$, $C_{3-8}$cycloalkyl, or CH$_2$—$C_{3-8}$cycloalkyl, and $Z^3$ is Br, I, or OTs, in the presence of a base such as cesium carbonate, and the like, in a suitable solvent such as DMF, to a compound of formula (X) and (XI), where $R^1$ is isopropyl, cyclobutyl, cyclopentyl, cyclobutylmethyl, or 2-methoxyethyl.

A compound of formula (IX), where $R^3$ is CF$_3$, is also treated with an alkylating reagent of formula $(R^1)_3O^+BF_4^-$, where is $R^1$ is methyl or ethyl, in a suitable solvent such as EtOAc to provide a compound of formula (X) and (XI), where $R^1$ is methyl or ethyl.

A compound of formula (IX), where $R^3$ is CF$_3$, is also treated with sodium chlorodifluoroacetate in the presence of a suitable base such as Cs$_2$CO$_3$ while employing conventional heating at a temperature such as 95° C. in a solvent such as DMF to provide a compound of formula (X) and (XI), where $R^1$ is difluoromethyl.

A compound of formula (IX), where $R^3$ is $CF_3$, is also treated with a halopyridine such as 2-fluoropyridine in the presence of suitable base such as $K_2CO_3$, while employing conventional heating, at a temperature such as 80° C., in a suitable solvent such as DMSO, to provide a compound of formula (X) and (XI), where $R^1$ is 2-pyridyl.

A compound of formula (IX), where $R^3$ is $CF_3$, is also treated with 2-(trimethylsilyl)phenyl trifluoromethanesulfonate in the presence of a fluoride source such as NaF and/or CsF in a suitable solvent such as acetonitrile to to provide a compound of formula (X) and (XI), where $R^1$ is phenyl.

A compound of formula (XI), where $R^1$ is $C_{1-5}$alkyl, $CH_2CH_2OCH_3$, $C_{3-8}$cycloalkyl, or $CH_2$—$C_{3-8}$cycloalkyl and $R^3$ is $CF_3$, is treated with an electrophilic bromide source such as bromine, in a suitable solvent such as AcOH or concentrated sulfuric acid, in the presence of an oxidant such as sodium metaperiodate, employing conventional heating at temperatures ranging from rt to 70° C. to provide a compound of formula (XII).

SCHEME 5

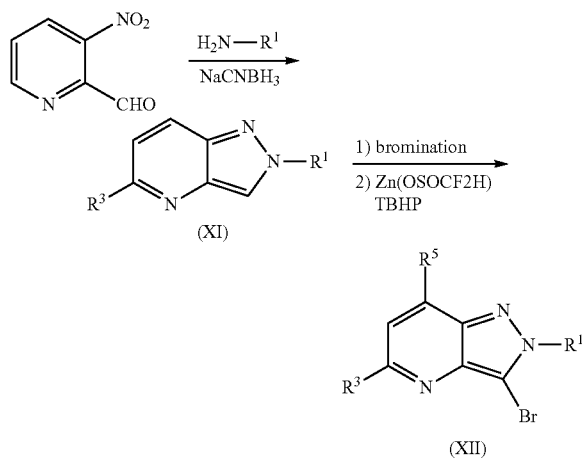

According to SCHEME 5, a compound of formula (XII), where $R^1$ is $C_{1-5}$alkyl, $C_{3-8}$cycloalkyl, or $CH_2$—$C_{3-8}$cycloalkyl, $R^3$ is H or $CF_2H$, and $R^5$ is H or $CF_2H$ may be prepared from commercially available 3-nitropyridine-2-carbaldehyde. 3-Nitropyridine-2-carbaldehyde may be treated with a primary amine of formula $H_2N$—$R^2$, where $R^1$ is $C_{1-5}$alkyl, in the presence of a reducing agent such as sodium cyanoborohydride, a dehydrating agent such as molecular sieves, in a suitable solvent such as acetic acid, may provide a bicyclic compound of formula (XI), where $R^1$ is $C_{1-5}$alkyl and $R^3$ is H. A compound of formula (XI), where $R^1$ is $C_{1-5}$alkyl and $R^3$ is H, may be treated with an electrophilic bromide source such as bromine, in a suitable solvent such as AcOH, employing conventional heating at temperatures ranging from rt to 70° C., may provide a compound of formula (XII). A compound of formula (XII) may further be treated with zinc difluoromethanesulfinate in the presence of a suitable oxidizing agent such as tert-butyl hydroperoxide, in a suitable solvent system such as DCM and water, may provide a compound of formula (XII), where $R^1$ is $C_{1-5}$alkyl, $C_{3-8}$cycloalkyl, or $CH_2$—$C_{3-8}$cycloalkyl, $R^3$ is H or $CF_2H$, $R^5$ is H or $CF_2H$, and its separable isomers.

SCHEME 6

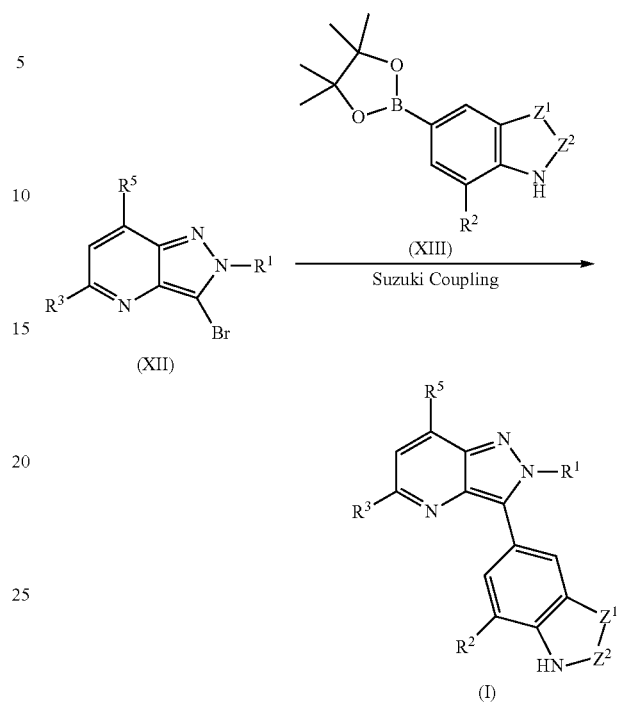

According to SCHEME 6, a compound of Formula (I), where $R^2$ is hydrogen, halogen, or $CH_3$, $R^1$ is $C_{1-5}$alkyl, $C_{1-5}$haloalkyl, $CH_2CH_2OCH_3$, $C_{3-8}$cycloalkyl, $CH_2$—$C_{3-8}$cycloalkyl, phenyl or pyridyl, $R^3$ is $CF_3$, $R^5$ is H or $CHF_2$, and —$Z^1$—$Z^2$— taken together form a group consisting of —CH=N—, —$CH_2$—C(=O)—, —S—C(=O), or —NH—C(=O)—, is prepared from a pyrazolopyridine compound of formula (XIV), where $R^3$ is $CF_3$. A compound of formula (XII) is treated with a commercially available or synthetically accessible boronic ester of formula (XIII), where $R^1$ and —$Z^1$—$Z^2$— are defined as above, in the presence of a suitable palladium catalyst such as $Pd(PPh_3)_4$, $Pd(dppf)Cl_2$, and the like, a base such as $Na_2CO_3$, $K_2CO_3$, and the like, employing conventional heating at temperatures ranging from 90 to 110° C., in a solvent system such as dioxane and water to provide a compound of Formula (I). In a similar fashion, a compound of Formula (I), where $R^3$ is H or $CF_2H$, may be prepared from a compound of formula (XII) where $R^3$ is H or $CF_2H$, employing Suzuki coupling methods previously described.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, $CH_3OH$, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

Examples

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge $^{18}C$ OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 m, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Intermediate 1: 5-Bromo-7-chloroindolin-2-one

To a cooled (0° C.) solution of 7-chloroindolin-2-one (1.0 g, 6.0 mmol) in TFA (11 mL) was added N-bromosuccinimide (1.0 g, 6.0 mmol) in portions. The reaction mixture was stirred at 0° C. for 6 h.

The solvent was removed in vacuo and the residue was diluted with DCM (25 mL) and concentrated, followed by a similar sequence with EtOAc. The crude product was triturated with ethanol to provide the title compound as a white solid (861 mg, 58% yield). MS (ESI): mass calcd. for $C_8H_5BrClNO$, 244.9; m/z found, 246.0 $[M+H]^+$. $^1H$ NMR (500 MHz, DMSO-$d_6$) δ 10.92 (s, 1H), 7.52-7.48 (m, 1H), 7.38 (d, J=1.2 Hz, 1H), 3.62 (s, 2H).

Intermediate 2: 5-Bromo-7-methylindolin-2-one

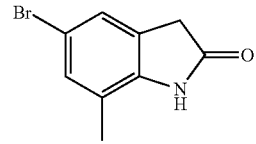

To a suspension of zinc dust (3.3 g, 51 mmol) in dry THF (60 mL) was added titanium tetrachloride (2.8 mL, 26 mmol) dropwise at rt under argon. The reaction mixture was heated to reflux for 2 h and then allowed to cool rt. To this mixture was added 5-bromo-7-methylindoline-2,3-dione (2.0 g, 8.3 mmol) in dry THF (40 mL) in portions. The reaction mixture was stirred at rt for 18 h. The reaction was quenched with 1 M HCl (40 mL). The mixture was diluted with EtOAc (60 mL) and the layers were separated. The organic layer was washed with brine (1×20 mL), dried over MgSO$_4$, filtered, and evaporated. The residue was purified by flash column chromatography (SiO$_2$; 10% EtOAc/CHCl$_3$). The product was then triturated with diisopropyl ether (10 mL) to give the title compound (1.0 g, 53% yield) as a pink crystalline solid. MS (ESI): mass calcd. for C$_9$H$_8$BrNO, 225.0; m/z found, 224.0 [M−H]$^-$.

Intermediate 3: 7-Methyl-5-(4,4,5,5-tetramethyl-1,3,2-dioxaborolan-2-yl)indolin-2-one

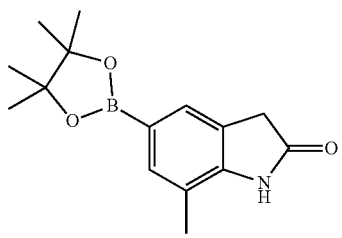 [SMILES: Cc1cc(B2OC(C)(C)C(C)(C)O2)cc2c1NC(=O)C2]

To a suspension of 5-bromo-7-methylindolin-2-one (Intermediate 2, 1.4 g, 6.19 mmol) in 1,4-dioxane (36 mL) were added bis(pinacolato)diboron (2.36 g, 9.29 mmol), KOAc (1.82 g, 18.5 mmol), and Pd(dppf)Cl$_2$ (227 mg, 0.31 mmol), and the reaction mixture was stirred at 100° C. for 18 h under argon. The reaction mixture was evaporated and the residue was purified by flash column chromatography (SiO$_2$; 50% EtOAc/hexanes). The product was triturated with diisopropyl ether (3 mL) to give the title compound (1.0 g, 59% yield) as a pale orange crystalline solid. MS (ESI): mass calcd. for C$_{16}$H$_{12}$ClF$_2$NO$_2$, 273.1; m/z found, 274.1 [M+H]$^+$. $^1$H NMR (300 MHz, DMSO-d$_6$) δ 10.55 (br s, 1H), 7.35-7.27 (m, 2H), 3.46 (s, 2H), 2.19 (s, 3H), 1.26 (s, 12H).

Intermediate 4: 7-Chloro-5-(4,4,5,5-tetramethyl-1,3,2-dioxaborolan-2-yl)indolin-2-one

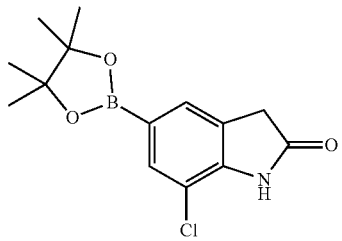 [SMILES: CC1(C)OB(c2cc(Cl)c3c(c2)CC(=O)N3)OC1(C)C]

The title compound was prepared in a manner analogous to Intermediate 3, substituting 5-bromo-7-chloroindolin-2-one (Intermediate 1) for 5-bromo-7-methylindolin-2-one (Intermediate 2). MS (ESI): mass calcd. for C$_{14}$H$_{17}$BClNO$_3$, 293.1; m/z found, 294.1 [M+H]$^+$. $^1$H NMR (400 MHz, DMSO-d$_6$) δ 10.94 (s, 1H), 7.43 (d, J=1.1 Hz, 1H), 7.41 (d, J=1.2 Hz, 1H), 3.60 (t, J=1.0 Hz, 2H), 1.28 (s, 12H).

Intermediate 5: 7-Methyl-5-(4,4,5,5-tetramethyl-1,3,2-dioxaborolan-2-yl)-1H-indazole

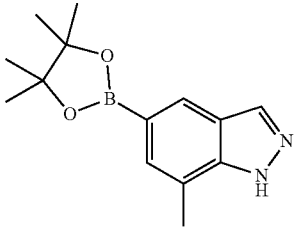 [SMILES: Cc1cc(B2OC(C)(C)C(C)(C)O2)cc2cn[nH]c12]

The title compound was prepared in a manner analogous to Intermediate 3, substituting 5-bromo-7-methyl-1H-indazole for 5-bromo-7-methylindolin-2-one (Intermediate 2). MS (ESI): mass calcd. for C$_{14}$H$_{19}$BN$_2$O$_2$, 258.1; m/z found, 259.1 [M+H]$^+$. $^1$H NMR (400 MHz, DMSO-d$_6$) δ 13.21 (s, 1H), 8.10 (d, J=1.3 Hz, 1H), 7.98 (s, 1H), 5.76 (s, 1H), 2.52 (s, 3H), 1.30 (s, 12H).

Intermediate 6: 7-Chloro-5-(4,4,5,5-tetramethyl-1,3,2-dioxaborolan-2-yl)-1H-indazole

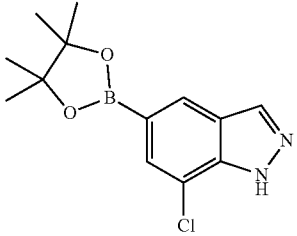 [SMILES: CC1(C)OB(c2cc(Cl)c3[nH]ncc3c2)OC1(C)C]

The title compound was prepared in a manner analogous to Intermediate 3, substituting 5-bromo-7-chloro-1H-indazole for 5-bromo-7-methylindolin-2-one (Intermediate 2). MS (ESI): mass calcd. for C$_{13}$H$_{16}$BClN$_2$O$_2$, 278.5; m/z found, 279.0 [M+H]$^+$. $^1$H NMR (400 MHz, DMSO-d$_6$) δ 13.72 (s, 1H), 8.25 (s, 1H), 8.18-8.05 (m, 1H), 7.56 (s, 1H), 1.31 (s, 12H).

Intermediate 7: Cyclobutyl 4-methylbenzenesulfonate

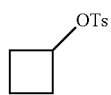

A solution of cyclobutanol (0.22 mL, 2.81 mmol) and p-toluenesulfonyl chloride (589 mg, 3.09 mmol) was stirred at rt overnight. The mixture was diluted with EtOAc and 1N HCl, and the aqueous layer was extracted with EtOAc (3×). The combined organic layers were washed with sat. aq. Cu$_2$SO$_4$ (3×), dried over Na$_2$SO$_4$, filtered, and concentrated in vacuo. The residue was purified by flash column chromatography (SiO$_2$; 0-20% EtOAc/hexanes) to afford the title compound as a colourless oil (521 mg, 82% yield). MS (ESI): mass calcd. for C$_{11}$H$_{14}$O$_3$S, 226.1; m/z found, 227.0 [M+H]$^+$. $^1$H NMR (500 MHz, CDCl$_3$) δ 7.78 (d, J=8.3 Hz, 2H), 7.33 (d, J=7.9 Hz, 2H), 4.86-4.66 (m, 1H), 2.44 (s, 3H), 2.23-2.09 (m, 4H), 1.79-1.69 (m, 1H), 1.55-1.44 (m, 1H).

Intermediate 8: 5-(Trifluoromethyl)-3a,7a-dihydro-1H-pyrazolo[4,3-b]pyridine

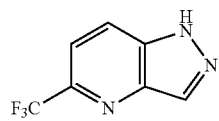

Step A: 2-Methyl-6-(trifluoromethyl)pyridin-3-amine

To a suspension of 3-amino-2-chloro-6-(trifluoromethyl)pyridine (9.0 g, 46 mmol) in 1,4-dioxane (144 mL) were added trimethylboroxine (19.0 mL, 136 mmol), Pd(dppf)Cl$_2$ (1.7 g, 2.3 mmol) and K$_2$CO$_3$ (19.0 g, 137 mmol). The reaction mixture was stirred at 110° C. for 18 h under argon. The mixture was diluted with EtOAc (36 mL), filtered and concentrated in vacuo. The residue was purified by flash column chromatography (SiO$_2$; 1% (2M NH$_3$ in EtOH)/CHCl$_3$). The residue was triturated with a mixture of n-hexane and diisopropyl ether (9:1, 10 mL) to give the title compound (6.5 g, 81% yield) as a tan crystalline solid. MS (ESI): mass calcd. for C$_7$H$_7$F$_3$N$_2$, 176.1; m/z found, 177.0 [M+H]$^+$.

Step B: 1-(5-(Trifluoromethyl)-3a,7a-dihydro-1H-pyrazolo[4,3-b]pyridin-1-yl)ethan-1-one To a solution of 2-methyl-6-(trifluoromethyl)pyridin-3-amine (2.5 g, 14 mmol) in CHCl$_3$ (65 mL) were added KOAc (1.7 g, 17.3 mmol), 1,4,7,10,13,16-hexaoxacyclooctadecane (18-Crown-6, 375 mg, 1.42 mmol), acetic anhydride (5.4 mL, 57 mmol) and isopentyl nitrite (3.8 mL, 28 mmol). The reaction mixture was stirred at 100° C. for 2 h, cooled to rt, filtered, and concentrated in vacuo. The residue was triturated with diisopropyl ether (5 mL) to give the title compound (1.6 g, 49% yield) as a pale orange crystalline solid, which was used directly in the next step without further purification.

Step C: 5-(Trifluoromethyl)-3a,7a-dihydro-1H-pyrazolo[4,3-b]pyridine

To a solution of 1-(5-(trifluoromethyl)-3a,7a-dihydro-1H-pyrazolo[4,3-b]pyridin-1-yl)ethan-1-one (1.30 g, 5.68 mmol) in MeOH (19 mL) and H$_2$O (1.2 mL) was added K$_2$CO$_3$ (1.27 g, 9.20 mmol). The reaction was stirred at rt for 30 min, and then heated to 50° C. for 1 h. After cooling to rt, the solvent was removed in vacuo, and the residue suspended in EtOAc. The suspension was washed with H$_2$O, and the organic layer was then dried over Na$_2$SO$_4$, filtered, and concentrated in vacuo. The crude solid was triturated in a mixture of DCM/hexanes to afford the title compound as a yellow solid (930 mg, 87% yield). MS (ESI): mass calcd. for C$_7$H$_4$F$_3$N$_3$, 187.0; m/z found, 188.0 [M+H]$^+$. $^1$H NMR (500 MHz, CDCl$_3$) δ 10.68 (s, 1H), 8.49 (d, J=1.1 Hz, 1H), 8.04 (d, J=8.7 Hz, 1H), 7.73 (d, J=8.8 Hz, 1H).

Intermediate 9: 2-Phenyl-5-(trifluoromethyl)-2H-pyrazolo[4,3-b]pyridine

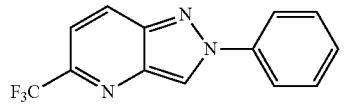

To a solution of 5-(trifluoromethyl)-3a,7a-dihydro-1H-pyrazolo[4,3-b]pyridine (Intermediate 8, 75 mg, 0.40 mmol) and 2-(trimethylsilyl)phenyl trifluoromethanesulfonate (97.3 µL, 0.40 mmol) in acetonitrile (3.0 mL) was added NaF (25 mg, 0.60 mmol) and CsF (152 mg, 1.02 mmol). The mixture was stirred at rt under an atmosphere of N$_2$ for 22 h before filtering over a pad of Celite. The Celite pad was washed with DCM and the filtrate was concentrated in vacuo. The residue purified by flash column chromatography (SiO$_2$; 0-10% EtOAc/hexanes) to afford the title compound (32 mg, 30% yield). $^1$H NMR (500 MHz, CDCl$_3$) δ 8.84 (s, 1H), 8.31 (d, J=9.0 Hz, 1H), 7.96-7.92 (m, 2H), 7.63-7.57 (m, 3H), 7.54-7.48 (m, 1H).

Intermediate 10: 2-(Difluoromethyl)-5-(trifluoromethyl)pyrazolo[4,3-b]pyridine

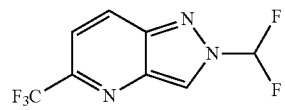

To a suspension of Cs$_2$CO$_3$ (600 mg, 1.84 mmol) in DMF (1.5 mL) were added 5-(trifluoromethyl)-3a,7a-dihydro-1H-pyrazolo[4,3-b]pyridine (Intermediate 8, 100 mg, 0.534 mmol) and sodium chlorodifluoroacetate (245 mg, 1.61 mmol) The reaction mixture was stirred at 95° C. for 1 h and then allowed to cool to rt. To the mixture was added water (10 mL) and the layers were separated. The aqueous layer was extracted with DCM (2×5 mL). The combined organic layers were washed with water (1×5 mL) and brine (1×4 mL), dried over MgSO$_4$, filtered, and concentrated in vacuo. The residue was purified by flash column chromatography (SiO$_2$; 100% toluene) to give the title compound (11 mg, 8% yield) as a white crystalline solid. $^1$H NMR (300 MHz, DMSO-d$_6$) δ 9.57 (s, 1H), 8.59 (d, J=9.2 Hz, 1H), 8.27 (t, J=58.6 Hz, 1H), 7.85 (d, J=9.2 Hz, 1H).

Intermediate 11: 2-Isopropyl-5-(trifluoromethyl)-2H-pyrazolo[4,3-b]pyridine

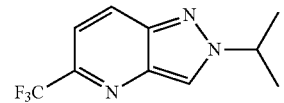

To a solution of 5-(trifluoromethyl)-3a,7a-dihydro-1H-pyrazolo[4,3-b]pyridine (Intermediate 8, 345 mg, 1.84 mmol) in dry DMF (8.7 mL) were added 2-iodopropane (550 μL, 5.51 mmol) and Cs₂CO₃ (1.2 g, 3.7 mmol). The reaction mixture was stirred at rt for 54 h. The mixture was diluted with toluene (15 mL), filtered and concentrated in vacuo. The resulting residue was purified by flash column chromatography (SiO₂; 5% EtOAc/toluene) to give the title compound (160 mg, 37% yield) as a pale yellow crystalline solid. ¹H NMR (300 MHz, DMSO-d₆) δ 9.03 (s, 1H), 8.40 (d, J=9.0 Hz, 1H), 7.68 (d, J=9.0 Hz, 1H), 5.07-4.87 (m, 1H), 1.60 (d, J=6.7 Hz, 6H).

Intermediate 12: 2-Cyclobutyl-5-(trifluoromethyl)-2H-pyrazolo[4,3-b]pyridine

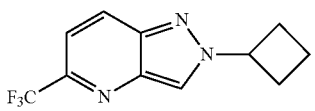

The title compound was prepared in an analogous manner to Intermediate 11, substituting cyclobutyl 4-methylbenzenesulfonate (Intermediate 7) for 5-(trifluoromethyl)-3a,7a-dihydro-1H-pyrazolo[4,3-b]pyridine (Intermediate 8). MS (ESI): mass calcd. for C₁₁H₁₀F₃N₃, 241.1; m/z found, 242.0 [M+H]⁺.

Intermediate 13: 2-Cyclopentyl-5-(trifluoromethyl)-2H-pyrazolo[4,3-b]pyridine

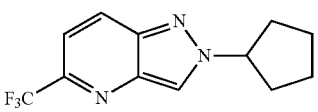

The title compound was prepared in an analogous manner to Intermediate 11, substituting iodocyclopentane for 5-(trifluoromethyl)-3a,7a-dihydro-1H-pyrazolo[4,3-b]pyridine (Intermediate 8). MS (ESI): mass calcd. for C₁₂H₁₂F₃N₃, 255.1; m/z found, 256.1 [M+H]⁺.

Intermediate 14: 2-(Cyclobutylmethyl)-5-(trifluoromethyl)-2H-pyrazolo[4,3-b]pyridine

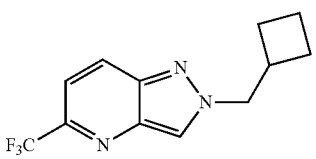 [SMILES: FC(F)(F)c1ccc2nn(CC3CCC3)cc2n1]

The title compound was prepared in an analogous manner to Intermediate 11, substituting (bromomethyl)cyclobutane for 5-(trifluoromethyl)-3a,7a-dihydro-1H-pyrazolo[4,3-b]pyridine (Intermediate 8). MS (ESI): mass calcd. for C₁₂H₁₂F₃N₃, 255.1; m/z found, 256.0 [M+H]⁺.

Intermediate 15: 2-(2-Methoxyethyl)-5-(trifluoromethyl)-2H-pyrazolo[4,3-b]pyridine

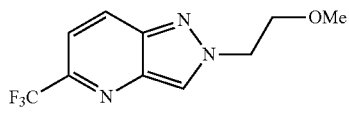

The title compound was prepared in an analogous manner to Intermediate 11, substituting 1-bromo-2-methoxyethane for 5-(trifluoromethyl)-3a,7a-dihydro-1H-pyrazolo[4,3-b]pyridine (Intermediate 8). MS (ESI): mass calcd. for C₁₀H₁₀F₃N₃O, 245.1; m/z found, 246.0 [M+H]⁺.

Intermediate 16: 2-Methyl-5-(trifluoromethyl)-2H-pyrazolo[4,3-b]pyridine

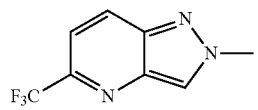

To a solution of 5-(trifluoromethyl)-3a,7a-dihydro-1H-pyrazolo[4,3-b]pyridine (Intermediate 8, 100 mg, 0.53 mmol) in EtOAc (1.6 mL) was added trimethyloxonium tetrafluoroborate (103 mg, 0.70 mmol), and the reaction was stirred under an N₂ atmosphere overnight. The mixture was diluted with EtOAc and then washed with sat. aq. NaHCO₃. The aqueous layer was extracted with EtOAc (2×), and the combined organics dried over Na₂SO₄ and filtered. The filtrate was concentrated in vacuo, and the residue purified by flash column chromatography (SiO₂; 0-100% EtOAc/hexanes) to afford the title compound as a white solid (86.1 mg, 80% yield). MS (ESI): mass calcd. for C₈H₆F₃N₃, 201.1; m/z found, 202.0 [M+H]⁺.

Intermediate 17: 2-Ethyl-5-(trifluoromethyl)-2H-pyrazolo[4,3-b]pyridine

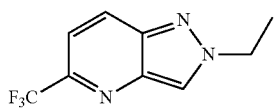

The title compound was prepared in an analogous manner to Intermediate 16, substituting triethyloxonium hexafluorophosphate for trimethyloxonium tetrafluoroborate. MS (ESI): mass calcd. for C₉H₈F₃N₃, 215.1; m/z found, 216.0 [M+H]⁺. ¹H NMR (500 MHz, DMSO-d₆) δ 8.98 (s, 1H), 8.39 (d, J=9.0 Hz, 1H), 7.68 (d, J=9.0 Hz, 1H), 4.58 (q, J=7.3 Hz, 2H), 1.56 (t, J=7.3 Hz, 3H).

Intermediate 18: 2-(Pyridin-2-yl)-5-(trifluoromethyl)-2H-pyrazolo[4,3-b]pyridine

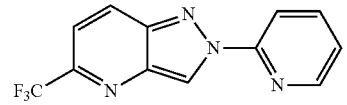

To a solution of 5-(trifluoromethyl)-3a,7a-dihydro-1H-pyrazolo[4,3-b]pyridine (Intermediate 8, 100 mg, 0.53 mmol) in DMSO (4 mL) was added K₂CO₃ (295 mg, 2.14 mmol), and the mixture was stirred at rt for 30 min. 2-fluoropyridine (0.14 mL, 1.6 mmol) was then added, and the reaction was heated at 80° C. for 2 days. After cooling to rt, the mixture was filtered, and to the filtrate were added DCM and 5% aqueous citric acid. The organic layer was then separated and washed successively washed with 5% aqueous citric acid, sat. aq. NaHCO₃, and brine. After drying over Na₂SO₄ and filtering, the filtrate was concentrated in vacuo. The crude residue was purified by flash column chromatography (SiO₂; 0-100% EtOAc/hexanes) to afford the title compound (19 mg, 13% yield). MS (ESI): mass calcd. for $C_{12}H_7F_3N_4$, 264.0; m/z found, 265.0 [M+H]⁺.

Intermediate 19: 6-(4,4,5,5-Tetramethyl-1,3,2-dioxaborolan-2-yl)benzo[d]thiazol-2(3H)-one

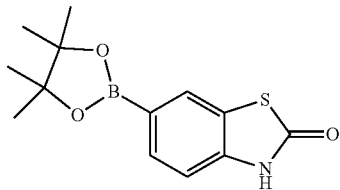 [SMILES: CC1(C)OB(c2ccc3[nH]c(=O)sc3c2)OC1(C)C]

To a solution of 6-bromobenzo[d]thiazol-2(3H)-one (1.0 g, 4.4 mmol) in DME (4.0 mL) were added bis(pinacoloato)diboron (1.1 g, 4.3 mmol), Pd₂(dba)₃ (119 mg, 0.13 mmol), butyldi-1-adamantylphosphine (140 mg, 0.39 mmol) and potassium acetate (1.3 g, 13 mmol). The reaction mixture was purged with nitrogen for 10 minutes and then heated at 65° C. for 16 h. After cooling to rt, the solvent was removed in vacuo. The crude residue was triturated with DCM and the filtrate was purified by FCC (SiO₂; 0-30% EtOAc/hexanes) to afford the title compound as a yellow solid (150 mg, 13% yield). MS (ESI): mass calcd. for $C_{13}H_{16}BNO_3S$, 277.1; m/z found, 278.2 [M+H]⁺. ¹H NMR (500 MHz, CDCl₃) δ 12.02 (s, 1H), 7.90-7.73 (m, 1H), 7.57 (dd, J=7.9, 1.2 Hz, 1H), 7.12 (dd, J=7.9, 0.6 Hz, 1H), 1.29 (s, 12H).

Intermediate 20: 2-Isopropylpyrazolo[4,3-b]pyridine

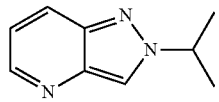

To a suspension of 3-nitropyridine-2-carbaldehyde (200 mg, 1.3 mmol) in 1,4-dioxane (8.0 mL) were added isopropylamine (140 µL, 1.6 mmol) and 4 Å molecular sieves (400 mg). The reaction mixture was stirred at rt for 2 h. The reaction mixture was cooled to 10° C. and sodium cyanoborohydride (110 mg, 1.8 mmol) and acetic acid (120 µL, 2.1 mmol) were added. The reaction mixture was stirred at 10° C. for 30 min and then at rt for 20 h, followed by heating at 100° C. for 24 h. The reaction mixture was cooled to room temperature, filtered through a pad of Celite and evaporated. The residue was purified by FCC (SiO₂; 50% EtOAc/hexanes) to afford the title compound as a dark yellow oil (46 mg, 22% yield). MS (ESI): mass calcd. for $C_9H_{11}N_3$, 161.1; m/z found, 162.1 [M+H]⁺. ¹H NMR (300 MHz, DMSO-d₆) δ 8.73-8.68 (m, 1H), 8.49 (dd, J=4.1, 1.5 Hz, 1H), 8.12-8.02 (m, 1H), 7.25 (dd, J=8.7, 4.1 Hz, 1H), 4.94-4.79 (m, 1H), 1.57 (d, J=6.7 Hz, 6H).

Intermediate 21: 3-Bromo-5-(difluoromethyl)-2-isopropyl-2H-pyrazolo[4,3-b]pyridine

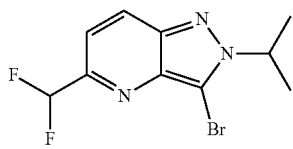 [SMILES: CC(C)n1nc2ccc(C(F)F)nc2c1Br]

Step A: 3-Bromo-2-isopropvlpyrazolo[4,3-b]pyridine hydrobromide

To a solution of 2-isopropylpyrazolo[4,3-b]pyridine (Intermediate 20, 170 mg, 1.1 mmol) in acetic acid (4.3 mL) was added bromine (147 µL, 2.9 mmol) and the reaction mixture was stirred at 70° C. for 4 h. To the reaction mixture was added additional bromine (74 µL, 1.4 mmol) and the reaction mixture was stirred at 70° C. for 4 h. To the reaction mixture was added a third portion of bromine (100 µL, 1.9 mmol) and the reaction mixture was stirred at 70° C. for 2 h. To the reaction mixture was added a fourth portion of bromine (100 µL, 1.9 mmol) and the reaction mixture was stirred at 70° C. for 2 h. The reaction mixture was cooled to rt and poured into ice water (20 mL). The aqueous layer was decanted from the precipitate. The crude product was triturated with diethyl ether (10 mL) to afford the title compound as a brown solid (247 mg, 72% yield). MS (ESI): mass calcd. for $C_9H_{10}BrN_3$, 239.0; m/z=240.0 [M+H]⁺. ¹H NMR (500 MHz, DMSO-d₆) δ 8.57 (dd, J=4.0, 1.4 Hz, 1H), 8.17 (dd, J=8.7, 1.4 Hz, 1H), 7.36 (dd, J=8.7, 4.1 Hz, 1H), 5.52-4.98 (m, 1H), 5.17-5.06 (m, 1H), 1.55 (d, J=6.6 Hz, 6H).

Step B: 3-Bromo-5-(difluoromethyl)-2-isopropylpyrazolo[4,3-b]pyridine

To a solution of 3-bromo-2-isopropylpyrazolo[4,3-b]pyridine hydrobromide (130 mg, 0.41 mmol) in a mixture of DCM (2 mL) and water (800 µL) was added zinc difluoromethanesulfinate (240 mg, 0.812 mmol). The reaction mixture was cooled to 0° C. and tert-butyl hydroperoxide (70% aqueous solution, 167 µL, 1.7 mmol) was added dropwise over 5 min with vigorous stirring. The reaction mixture was stirred at 0° C. for 30 min and then diluted with DCM (3 mL) and saturated aqueous sodium bicarbonate solution (3 mL). The layers were separated, and the aqueous layer was extracted with DCM (3×2 mL). The combined organic layers were dried over magnesium sulfate, filtered and evaporated. The crude product was purified by FCC (SiO₂; 10% EtOAc/hexanes) to afford the title compound as a white solid (9.3 mg, 8% yield), along with 3-bromo-7-(difluoromethyl)-2-isopropylpyrazolo[4,3-b]pyridine (Intermediate 22, 20 mg, 17% yield) and 3-bromo-5,7-bis(difluoromethyl)-2-isopropylpyrazolo[4,3-b]pyridine (Intermediate 23, 7.3 mg, 5% yield). MS (ESI): mass calcd. for $C_{10}H_{10}BrF_2N_3$, 289.0; found, m/z=290.0 [M+H]⁺. ¹H NMR (500 MHz, DMSO-d₆) δ 8.38 (d, J=9.0 Hz, 1H), 7.62 (d, J=8.9 Hz, 1H), 7.05 (t, J=54.8 Hz, 1H), 5.21-5.10 (m, 1H), 1.57 (d, J=6.6 Hz, 6H).

Intermediate 22: 3-Bromo-7-(difluoromethyl)-2-isopropylpyrazolo[4,3-b]pyridine

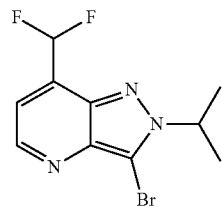 [SMILES: CC(C)n1nc2c(C(F)F)ccnc2c1Br]

The title compound was isolated as a white solid (20 mg, 17% yield) in Step B of the synthesis of Intermediate 21. MS (ESI): mass calcd. for $C_{10}H_{10}BrF_2N_3$, 289.0; found, m/z=290.0 $[M+H]^+$. $^1H$ NMR (500 MHz, DMSO-$d_6$) δ 8.70 (d, J=4.2 Hz, 1H), 7.56-7.53 (m, 1H), 7.45 (t, J=54.0 Hz, 1H), 5.19-5.11 (m, 1H), 1.57 (d, J=6.6 Hz, 6H).

Intermediate 23: 3-Bromo-5,7-bis(difluoromethyl)-2-isopropylpyrazolo[4,3-b]pyridine

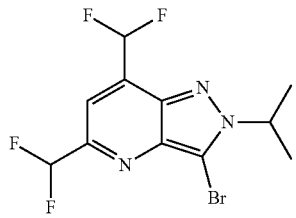 [SMILES: CC(C)n1nc2c(C(F)F)cc(C(F)F)nc2c1Br]

The title compound was isolated as a white solid (7.3 mg, 5% yield) in Step B of the synthesis of Intermediate 21. MS (ESI): mass calcd. for $C_{11}H_{10}BrF_4N_3$, 339.0; found, m/z=340.0 $[M+H]^+$. $^1H$ NMR (500 MHz, DMSO-$d_6$) δ 7.81-7.76 (m, 1H), 7.52 (t, J=53.8 Hz, 1H), 7.14 (t, J=54.5 Hz, 1H), 5.25-5.14 (m, 1H), 1.58 (d, J=6.6 Hz, 6H).

Example 1: 5-(2-Methyl-5-(trifluoromethyl)-2H-pyrazolo[4,3-b]pyridin-3-yl)-1,3-dihydro-2H-benzo[d]imidazol-2-one

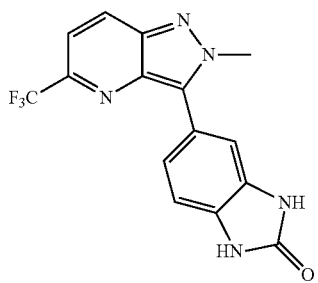 [SMILES: Cn1nc2ccc(C(F)(F)F)nc2c1-c1ccc2[nH]c(=O)[nH]c2c1]

Step A: 3-Bromo-2-methyl-5-(trifluoromethyl)-2H-pyrazolo[4,3-b]pyridine

To a suspension of 2-methyl-5-(trifluoromethyl)-2H-pyrazolo[4,3-b]pyridine (Intermediate 16, 40 mg, 0.20 mmol) in AcOH (1.0 mL) was added bromine (23 μL, 0.44 mmol), and the reaction was stirred at 70° C. for 3 h. After cooling to rt, the solvent was removed in vacuo, and the residue dissolved in DCM. The solution was washed once with water, and then the aqueous layer extracted with DCM (2×). The combined organics were dried over $Na_2SO_4$, filtered, and concentrated in vacuo. The residue was used without further purification.

Step B: 5-(2-Methyl-5-(trifluoromethyl)-2H-pyrazolo[4,3-b]pyridin-3-yl)-1,3-dihydro-2H-benzo[d]imidazol-2-one A microwave vial was charged with 3-bromo-2-methyl-5-(trifluoromethyl)-2H-pyrazolo[4,3-b]pyridine (53 mg, 0.19 mmol), 5-(4,4,5,5-tetramethyl-1,3,2-dioxaborolan-2-yl)-1,3-dihydro-2H-benzo[d]imidazol-2-one (74 mg, 0.28 mmol), Pd(PPh$_3$)$_4$ (22 mg, 0.019 mmol), sat. aq. $Na_2CO_3$ (0.65 mL), and 1,4-dioxane (2.6 mL). The headspace was evacuated and immediately refilled with $N_2$ (3×). The reaction vial was capped, sealed, and heated in an oil bath at 90° C. for 18 h. After cooling to rt, the mixture was diluted with EtOAc and $H_2O$. The aqueous layer was extracted with EtOAc (2×), and the combined organics dried over $Na_2SO_4$, filtered, and concentrated in vacuo. The crude residue was purified by reverse-phase HPLC on a XBridge C18 column (5 m, 100×4.6 mm), mobile phase of 10-100% ACN in 20 mM $NH_4OH$, to afford the title compound as a white solid (24 mg, 37% yield). MS (ESI): mass calcd. for $C_{15}H_{10}F_3N_5O$, 333.1; m/z found, 334.0 $[M+H]^+$. $^1H$ NMR (600 MHz, DMSO-$d_6$) δ 10.86 (s, 2H), 8.38 (d, J=8.8 Hz, 1H), 7.72 (d, J=9.0 Hz, 1H), 7.36 (d, J=1.7 Hz, 2H), 7.17 (d, J=8.7 Hz, 1H), 4.27 (s, 3H).

Example 2: 7-Methyl-5-(2-methyl-5-(trifluoromethyl)-2H-pyrazolo[4,3-b]pyridin-3-yl)indolin-2-one

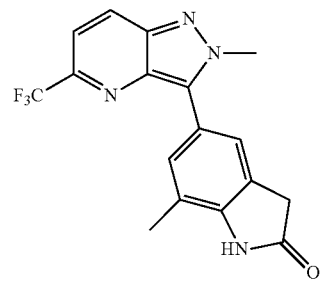

Step A: 3-Bromo-2-methyl-5-(trifluoromethyl)-2H-pyrazolo[4,3-b]pyridine

To a solution of 2-methyl-5-(trifluoromethyl)-2H-pyrazolo[4,3-b]pyridine (Intermediate 16, 130 mg, 0.65 mmol) in AcOH (3 mL) was added bromine (89 μL, 1.7 mmol) and the reaction mixture was stirred at 70° C. for 2 h. To the reaction mixture was added additional bromine (15 μL, 0.3 mmol) and stirring was maintained for 18 h. The reaction mixture was poured into ice water (15 mL). The precipitate was collected and washed with water (3×2 mL) and with n-hexane (1×300 μL) to give the title compound (110 mg, 60% yield) as an off-white crystalline solid. MS (ESI): mass calcd. for $C_8H_5BrF_3N_3$, 279.0; m/z found, 279.7 $[M+H]^+$. $^1H$ NMR (500 MHz, DMSO-$d_6$) δ 8.44 (d, J=9.0 Hz, 1H), 7.76 (d, J=9.0 Hz, 1H), 4.29 (s, 3H).

Step B: 7-Methyl-5-(2-methyl-5-(trifluoromethyl)-2H-pyrazolo[4,3-b]pyridin-3-yl)indolin-2-one To a solution of 3-bromo-2-methyl-5-(trifluoromethyl)pyrazolo[4,3-b]pyridine (95 mg, 0.34 mmol) in a mixture of 1,4-dioxane and water (10:1, 1.3 mL) were added 7-methyl-5-(4,4,5,5-tetramethyl-1,3,2-dioxaborolan-2-yl)indolin-2-one (Intermediate 3, 121 mg, 0.44 mmol), Pd(dppf)Cl$_2$ (25 mg, 0.03 mmol), and potassium carbonate (118 mg, 0.85 mmol). The reaction mixture was stirred at 110° C. for 18 h under argon. The mixture was diluted with CHCl$_3$ (10 mL), filtered, and evaporated in vacuo. The residue was purified by flash column chromatography (SiO$_2$; 50% EtOAc/CHCl$_3$). The product was triturated with diethyl ether (2 mL) to give the title compound (51 mg, 43% yield) as a tan crystalline solid. MS (ESI): mass calcd. for C$_{17}$H$_{13}$F$_3$N$_4$O, 346.1.1; m/z found, 347.1 [M+H]$^+$. $^1$H NMR (500 MHz, DMSO-d$_6$) δ 10.70 (s, 1H), 8.38 (d, J=9.0 Hz, 1H), 7.71 (d, J=9.0 Hz, 1H), 7.47-7.44 (m, 1H), 7.43-7.39 (m, 1H), 4.25 (s, 3H), 3.63 (s, 2H), 2.31 (s, 3H).

Example 3: 5-[2-(Difluoromethyl)-5-(trifluoromethyl)pyrazolo[4,3-b]pyridin-3-yl]-7-methyl-indolin-2-one

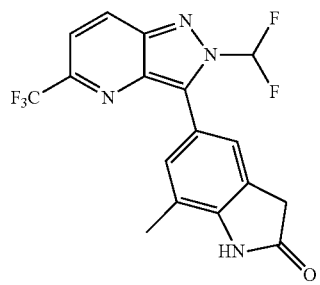

Step A: 3-Bromo-2-(difluoromethyl)-5-(trifluoromethyl)pyrazolo[4,3-b]pyridine

To a cooled (0° C.) solution of bromine (8.0 μL, 0.2 mmol) in conc. sulfuric acid (160 μL, 3.0 mmol) was added 2-(difluoromethyl)-5-(trifluoromethyl)pyrazolo[4,3-b]pyridine (Intermediate 10, 25 mg, 0.11 mmol). The reaction mixture was stirred at rt for 30 min. To the reaction mixture was added sodium metaperiodate (6.2 mg, 0.03 mmol) and stirring was maintained at rt for 40 min. The mixture was poured into ice water (10 mL) and made basic (pH 10) by the addition of 10% aqueous NaOH solution. The resulting precipitate was collected and washed with water (3×1 mL) to give the title compound (14 mg, 42% yield) as a white crystalline solid. $^1$H NMR (500 MHz, DMSO-d$_6$) δ 8.62 (d, J=9.2 Hz, 1H), 8.39 (t, J=56.6 Hz, 1H), 7.90 (d, J=9.2 Hz, 1H).

Step B: 5-[2-(Difluoromethyl)-5-(trifluoromethyl)pyrazolo[4,3-b]pyridin-3-yl]-7-methyl-indolin-2-one The title compound was prepared in a manner analogous to Example 2, substituting 3-bromo-2-(difluoromethyl)-5-(trifluoromethyl)pyrazolo[4,3-b]pyridine for 3-bromo-2-methyl-5-(trifluoromethyl)pyrazolo[4,3-b]pyridine in Step B. $^1$H NMR (500 MHz, DMSO-d$_6$) δ 10.79 (s, 1H), 8.56 (d, J=9.1 Hz, 1H), 8.15 (t, J=56.8 Hz, 1H), 7.86 (d, J=9.1 Hz, 1H), 7.40-7.36 (m, 1H), 7.36-7.31 (m, 1H), 3.64 (s, 2H), 2.31 (s, 3H).

Example 4: 5-(2-Ethyl-5-(trifluoromethyl)-2H-pyrazolo[4, 3-b]pyridin-3-yl)-1,3-dihydro-2H-benzo[d]imidazol-2-one

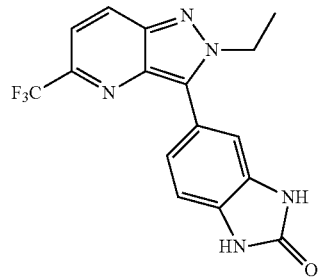 [SMILES: CCn1nc2ccc(C(F)(F)F)nc2c1-c1ccc2[nH]c(=O)[nH]c2c1]

The title compound was prepared in a manner analogous to Example 1, substituting 2-ethyl-5-(trifluoromethyl)-2H-pyrazolo[4,3-b]pyridine (Intermediate 17) for 2-methyl-5-(trifluoromethyl)-2H-pyrazolo[4,3-b]pyridine (Intermediate 16) in Step A. MS (ESI): mass calcd. for C$_{16}$H$_{12}$F$_3$N$_5$O, 347.1; m/z found, 348.0 [M+H]$^+$. $^1$H NMR (600 MHz, DMSO-d$_6$) δ 10.86 (d, J=37.5 Hz, 2H), 8.41 (d, J=9.3 Hz, 1H), 7.71 (d, J=9.0 Hz, 1H), 7.31-7.22 (m, 2H), 7.17 (d, J=8.5 Hz, 1H), 4.55 (q, J=7.2 Hz, 2H), 1.51 (t, J=7.2 Hz, 3H).

Example 5: 5-(2-Isopropyl-5-(trifluoromethyl)-2H-pyrazolo[4,3-b]pyridin-3-yl)-1,3-dihydro-2H-benzo[d]imidazol-2-one

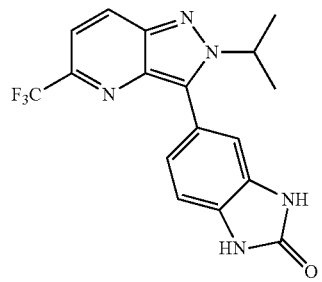 [SMILES: CC(C)n1nc2ccc(C(F)(F)F)nc2c1-c1ccc2[nH]c(=O)[nH]c2c1]

The title compound was prepared in a manner analogous to Example 1, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A. MS (ESI): mass calcd. for C$_{17}$H$_{14}$F$_3$N$_5$O, 361.1; m/z found, 362.0 [M+H]$^+$. $^1$H NMR (400 MHz, MeOD) δ 8.27 (d, J=9.0 Hz, 1H), 7.64 (d, J=9.0 Hz, 1H), 7.31 (s, 1H), 7.30-7.22 (m, 2H), 5.12 (dt, J=13.2, 6.6 Hz, 1H), 1.62 (d, J=6.6 Hz, 6H).

Example 6: 5-(2-(Cyclobutylmethyl)-5-(trifluoromethyl)-2H-pyrazolo[4,3-b]pyridin-3-yl)-1,3-dihydro-2H-benzo[d]imidazol-2-one

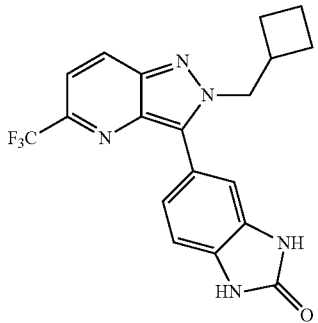 [SMILES: O=c1[nH]c2ccc(-c3c4nc(C(F)(F)F)ccc4nn3CC3CCC3)cc2[nH]1]

The title compound was prepared in a manner analogous to Example 1, substituting 2-(cyclobutylmethyl)-5-(trifluoromethyl)-2H-pyrazolo[4,3-b]pyridine (Intermediate 14) for 2-methyl-5-(trifluoromethyl)-2H-pyrazolo[4,3-b]pyridine (Intermediate 16) in Step A. MS (ESI): mass calcd. for $C_{19}H_{16}F_3N_{5O}$, 387.1; m/z found, 388.0 [M+H]$^+$. $^1$H NMR (400 MHz, MeOD) δ 8.26 (d, J=9.0 Hz, 1H), 7.65 (d, J=9.0 Hz, 1H), 7.38-7.29 (m, 2H), 7.29-7.22 (m, 1H), 4.61 (d, J=7.4 Hz, 2H), 2.92 (dt, J=14.8, 7.6 Hz, 1H), 2.05-1.67 (m, 6H).

Example 7: 5-(2-Cyclopentyl-5-(trifluoromethyl)-2H-pyrazolo[4, 3-b]pyridin-3-yl)-1,3-dihydro-2H-benzo[d]imidazol-2-one

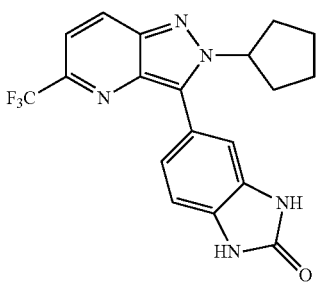 [SMILES: O=c1[nH]c2ccc(-c3c4nc(C(F)(F)F)ccc4nn3C3CCCC3)cc2[nH]1]

The title compound was prepared in a manner analogous to Example 1, substituting 2-cyclopentyl-5-(trifluoromethyl)-2H-pyrazolo[4,3-b]pyridine (Intermediate 13) for 2-methyl-5-(trifluoromethyl)-2H-pyrazolo[4,3-b]pyridine (Intermediate 16) in Step A. MS (ESI): mass calcd. for $C_{19}H_{16}F_3N_{5O}$, 387.1; m/z found, 388.0 [M+H]$^+$. $^1$H NMR (600 MHz, DMSO-d$_6$) δ 10.85 (d, J=52.0 Hz, 2H), 8.41 (d, J=9.0 Hz, 1H), 7.70 (d, J=9.0 Hz, 1H), 7.25-7.13 (m, 3H), 5.26-5.12 (m, 1H), 2.25-2.12 (m, 4H), 2.05-1.94 (m, 2H), 1.73-1.64 (m, 2H).

Example 8: 2-Cyclopentyl-3-(7-methyl-1H-indazol-5-yl)-5-(trifluoromethyl)-2H-pyrazolo[4,3-b]pyridine

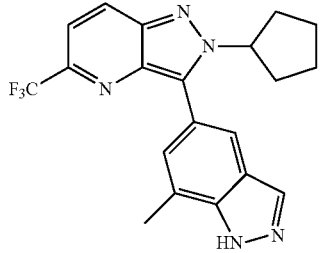 [SMILES: Cc1cc(-c2c3nc(C(F)(F)F)ccc3nn2C2CCCC2)cc2cn[nH]c12]

The title compound was prepared in a manner analogous to Example 1, substituting 2-cyclopentyl-5-(trifluoromethyl)-2H-pyrazolo[4,3-b]pyridine (Intermediate 13) for 2-methyl-5-(trifluoromethyl)-2H-pyrazolo[4,3-b]pyridine (Intermediate 16) in Step A, as well as 7-methyl-5-(4,4,5,5-tetramethyl-1,3,2-dioxaborolan-2-yl)-1H-indazole (Intermediate 5) for 5-(4,4,5,5-tetramethyl-1,3,2-dioxaborolan-2-yl)-1,3-dihydro-2H-benzo[d]imidazol-2-one and Pd(dppf)Cl$_2$—CH$_2$Cl$_2$ for Pd(PPh$_3$)$_4$ in Step B. MS (ESI): mass calcd. for $C_{20}H_{18}F_3N_5$, 385.2; m/z found, 386.0 [M+H]$^+$. $^1$H NMR (500 MHz, DMSO-d$_6$) δ 13.46 (s, 1H), 8.44 (d, J=8.7 Hz, 1H), 8.25 (s, 1H), 7.87 (s, 1H), 7.71 (d, J=9.0 Hz, 1H), 7.35 (s, 1H), 5.20-5.10 (m, 1H), 2.63 (s, 3H), 2.26-2.12 (m, 4H), 2.04-1.91 (m, 2H), 1.72-1.61 (m, 2H).

Example 9: 5-(2-Phenyl-5-(trifluoromethyl)-2H-pyrazolo[4,3-b]pyridin-3-yl)-1,3-dihydro-2H-benzo[d]imidazol-2-one

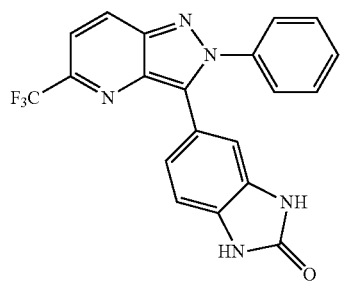 [SMILES: O=c1[nH]c2ccc(-c3c4nc(C(F)(F)F)ccc4nn3-c3ccccc3)cc2[nH]1]

The title compound was prepared in a manner analogous to Example 1, substituting 2-phenyl-5-(trifluoromethyl)-2H-pyrazolo[4,3-b]pyridine (Intermediate 9) for 2-methyl-5-(trifluoromethyl)-2H-pyrazolo[4,3-b]pyridine (Intermediate 16) in Step A. MS (ESI): mass calcd. for $C_{20}H_{12}F_3N_5O$, 395.1; m/z found, 396.0 [M+H]$^+$. $^1$H NMR (500 MHz, DMSO-d$_6$) δ 10.80 (d, J=37.1 Hz, 2H), 8.52 (d, J=9.1 Hz, 1H), 7.82 (d, J=9.0 Hz, 1H), 7.54 (s, 5H), 7.14 (s, 1H), 7.06-6.95 (m, 2H).

Example 10: 5-(2-Phenyl-5-(trifluoromethyl)-2H-pyrazolo[4,3-b]pyridin-3-yl)indolin-2-one

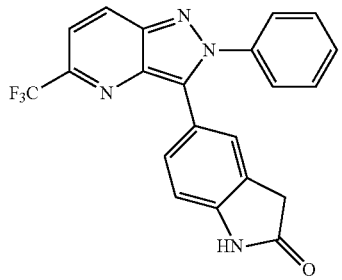 [SMILES: O=C1Cc2cc(-c3c4nc(C(F)(F)F)ccc4nn3-c3ccccc3)ccc2N1]

The title compound was prepared in a manner analogous to Example 1, substituting 2-phenyl-5-(trifluoromethyl)-2H-pyrazolo[4,3-b]pyridine (Intermediate 9) for 2-methyl-5-(trifluoromethyl)-2H-pyrazolo[4,3-b]pyridine (Intermediate 16) in Step A and 5-(4,4,5,5-tetramethyl-1,3,2-dioxaborolan-2-yl)indolin-2-one for 5-(4,4,5,5-tetramethyl-1,3,2-dioxaborolan-2-yl)-1,3-dihydro-2H-benzo[d]imidazol-2-one in Step B. MS (ESI): mass calcd. for $C_{21}H_{13}F_3N_4O$, 394.1; m/z found, 395.0 [M+H]$^+$. $^1$H NMR (500 MHz, CDCl$_3$) δ 8.38 (s, 1H), 8.28 (d, J=9.0 Hz, 1H), 7.63 (d, J=9.0 Hz, 1H), 7.55-7.46 (m, 6H), 7.37 (d, J=8.1 Hz, 1H), 6.87 (d, J=8.2 Hz, 1H), 3.55 (s, 2H).

Example 11: 3-(1H-Indazol-5-yl)-2-phenyl-5-(trifluoromethyl)-2H-pyrazolo[4,3-b]pyridine

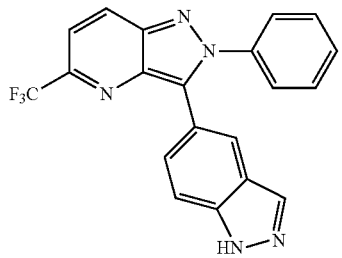 [SMILES: FC(F)(F)c1ccc2nn(-c3ccccc3)c(-c3ccc4[nH]ncc4c3)c2n1]

The title compound was prepared in a manner analogous to Example 1, substituting 2-phenyl-5-(trifluoromethyl)-2H-pyrazolo[4,3-b]pyridine (Intermediate 9) for 2-methyl-5-(trifluoromethyl)-2H-pyrazolo[4,3-b]pyridine (Intermediate 16) in Step A and 5-(4,4,5,5-tetramethyl-1,3,2-dioxaborolan-2-yl)-1H-indazole for 5-(4,4,5,5-tetramethyl-1,3,2-dioxaborolan-2-yl)-1,3-dihydro-2H-benzo[d]imidazol-2-one in Step B. MS (ESI): mass calcd. for $C_{20}H_{12}F_3N_5$, 379.1; m/z found, 380.0 [M+H]$^+$. $^1$H NMR (500 MHz, DMSO-d$_6$) δ 13.29 (s, 1H), 8.55 (d, J=9.1 Hz, 1H), 8.19 (s, 1H), 8.01 (s, 1H), 7.84 (d, J=9.0 Hz, 1H), 7.60 (d, J=8.7 Hz, 1H), 7.57-7.48 (m, 5H), 7.35 (dd, J=8.7, 1.6 Hz, 1H).

Example 12: 2-Cyclobutyl-3-(1H-indazol-5-yl)-5-(trifluoromethyl)-2H-pyrazolo[4,3-b]pyridine

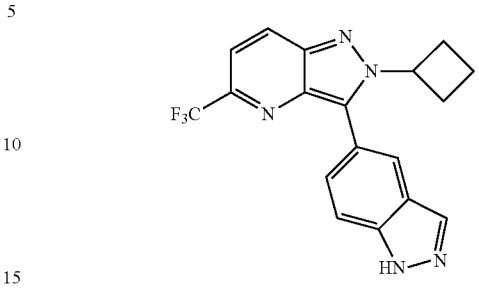

The title compound was prepared in a manner analogous to Example 1, substituting 2-cyclobutyl-5-(trifluoromethyl)-2H-pyrazolo[4,3-b]pyridine (Intermediate 12) for 2-methyl-5-(trifluoromethyl)-2H-pyrazolo[4,3-b]pyridine (Intermediate 16) in Step A and 5-(4,4,5,5-tetramethyl-1,3,2-dioxaborolan-2-yl)-1H-indazole for 5-(4,4,5,5-tetramethyl-1,3,2-dioxaborolan-2-yl)-1,3-dihydro-2H-benzo[d]imidazol-2-one in Step B. MS (ESI): mass calcd. for $C_{18}H_{14}F_3N_5$, 357.1; m/z found, 358.0 [M+H]$^+$. $^1$H NMR (500 MHz, DMSO-d$_6$) δ 13.37 (s, 1H), 8.49 (d, J=8.9 Hz, 1H), 8.27 (s, 1H), 8.06 (s, 1H), 7.80 (d, J=8.6 Hz, 1H), 7.75 (d, J=9.0 Hz, 1H), 7.60 (dd, J=8.6, 1.6 Hz, 1H), 5.39-5.29 (m, 1H), 2.89-2.74 (m, 2H), 2.53-2.42 (m, 2H), 1.96-1.82 (m, 2H).

Example 13: 3-(1H-Indazol-5-yl)-2-(2-methoxyethyl)-5-(trifluoromethyl)-2H-pyrazolo[4,3-b]pyridine

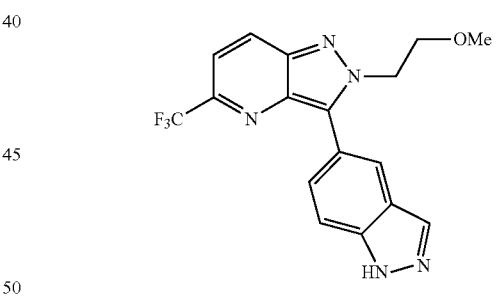

The title compound was prepared in a manner analogous to Example 1, substituting 2-(2-methoxyethyl)-5-(trifluoromethyl)-2H-pyrazolo[4,3-b]pyridine (Intermediate 15) for 2-methyl-5-(trifluoromethyl)-2H-pyrazolo[4,3-b]pyridine (Intermediate 16) in Step A and 5-(4,4,5,5-tetramethyl-1,3,2-dioxaborolan-2-yl)-1H-indazole for 5-(4,4,5,5-tetramethyl-1,3,2-dioxaborolan-2-yl)-1,3-dihydro-2H-benzo[d]imidazol-2-one in Step B. MS (ESI): mass calcd. for $C_{17}H_{14}F_3N_5O$, 361.1; m/z found, 362.0 [M+H]$^+$. $^1$H NMR (600 MHz, DMSO-d$_6$) δ 13.39 (s, 1H), 8.45 (d, J=9.0 Hz, 1H), 8.27 (s, 1H), 8.16 (s, 1H), 7.80 (d, J=8.6 Hz, 1H), 7.76 (d, J=9.0 Hz, 1H), 7.70 (dd, J=8.6, 1.5 Hz, 1H), 4.70 (t, J=5.2 Hz, 2H), 3.94 (t, J=5.2 Hz, 2H), 3.14 (s, 3H).

Example 14: 3-(1H-Indazol-5-yl)-2-(pyridin-2-yl)-5-(trifluoromethyl)-2H-pyrazolo[4,3-b]pyridine

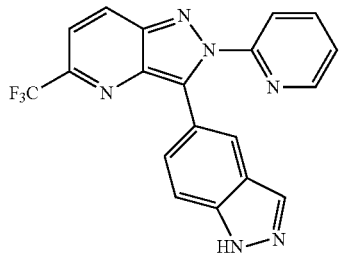 [SMILES: FC(F)(F)c1ccc2nn(-c3ccccn3)c(-c3ccc4[nH]ncc4c3)c2n1]

The title compound was prepared in a manner analogous to Example 1, substituting 2-(pyridin-2-yl)-5-(trifluoromethyl)-2H-pyrazolo[4,3-b]pyridine (Intermediate 18) for 2-methyl-5-(trifluoromethyl)-2H-pyrazolo[4,3-b]pyridine (Intermediate 16) in Step A and 5-(4,4,5,5-tetramethyl-1,3,2-dioxaborolan-2-yl)-1H-indazole for 5-(4,4,5,5-tetramethyl-1,3,2-dioxaborolan-2-yl)-1,3-dihydro-2H-benzo[d]imidazol-2-one in Step B. MS (ESI): mass calcd. for $C_{19}H_{11}F_3N_6$, 380.1; m/z found, 381.2 [M+H]$^+$. $^1$H NMR (500 MHz, DMSO-d$_6$) δ 13.27 (s, 1H), 8.57 (d, J=9.1 Hz, 1H), 8.46 (ddd, J=4.8, 1.9, 0.8 Hz, 1H), 8.18 (dd, J=1.5, 1.0 Hz, 1H), 8.17-8.12 (m, 1H), 7.99 (dt, J=1.6, 0.8 Hz, 1H), 7.91 (dt, J=8.0, 0.9 Hz, 1H), 7.86 (d, J=9.1 Hz, 1H), 7.63-7.56 (m, 2H), 7.34 (dd, J=8.7, 1.6 Hz, 1H).

Example 15: 2-Methyl-3-(7-methyl-1H-indazol-5-yl)-5-(trifluoromethyl)-2H-pyrazolo[4,3-b]pyridine

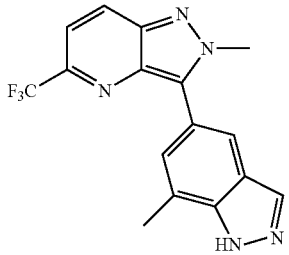 [SMILES: Cc1cc(-c2c3nc(C(F)(F)F)ccc3nn2C)cc2cn[nH]c12]

The title compound was prepared in a manner analogous to Example 2, substituting 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{16}H_{12}F_3N_5$, 331.1; m/z found, 332.1 [M+H]$^+$. $^1$H NMR (500 MHz, DMSO-d$_6$) δ 13.44 (br s, 1H), 8.41 (d, J=8.9 Hz, 1H), 8.25 (d, J=1.4 Hz, 1H), 8.01-7.99 (m, 1H), 7.73 (d, J=9.0 Hz, 1H), 7.54-7.51 (m, 1H), 4.28 (s, 3H), 2.63 (s, 3H).

Example 16: 3-(7-Chloro-1H-indazol-5-yl)-2-methyl-5-(trifluoromethyl)-2H-pyrazolo[4,3-b]pyridine

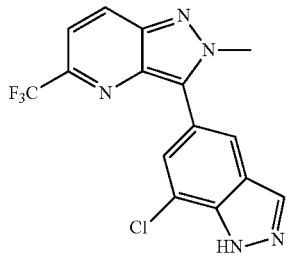 [SMILES: Cn1nc2ccc(C(F)(F)F)nc2c1-c1cc(Cl)c2[nH]ncc2c1]

The title compound was prepared in a manner analogous to Example 2, using 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{15}H_9ClF_3N_5$, 351.0; m/z found, 352.1 [M+H]$^+$. $^1$H NMR (500 MHz, DMSO-d$_6$) δ 13.93 (br s, 1H), 8.44 (d, J=9.0 Hz, 1H), 8.41-8.38 (m, 1H), 8.20 (d, J=1.3 Hz, 1H), 7.91 (d, J=1.3 Hz, 1H), 7.75 (d, J=8.9 Hz, 1H), 4.32 (s, 3H).

Example 17: 5-(2-Ethyl-5-(trifluoromethyl)-2H-pyrazolo[4,3-b]pyridin-3-yl)-7-methylindolin-2-one

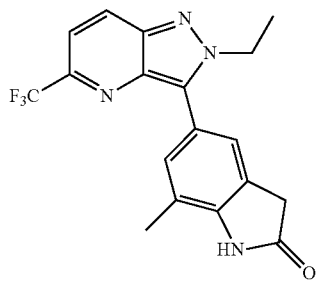 [SMILES: CCn1nc2ccc(C(F)(F)F)nc2c1-c1cc(C)c2c(c1)CC(=O)N2]

The title compound was prepared in a manner analogous to Example 2, substituting 2-ethyl-5-(trifluoromethyl)-2H-pyrazolo[4,3-b]pyridine (Intermediate 17) for 2-methyl-5-(trifluoromethyl)-2H-pyrazolo[4,3-b]pyridine (Intermediate 16) in Step A. MS (ESI): mass calcd. for $C_{17}H_{15}F_3N_4O$, 360.1; m/z found, 361.1 [M+H]$^+$. $^1$H NMR (500 MHz, DMSO-d$_6$) δ 10.70 (s, 1H), 8.40 (d, J=9.0 Hz, 1H), 7.70 (d, J=9.0 Hz, 1H), 7.37-7.33 (m, 1H), 7.33-7.29 (m, 1H), 4.52 (q, J=7.3 Hz, 2H), 3.62 (s, 2H), 2.31 (s, 3H), 1.49 (t, J=7.2 Hz, 3H).

Example 18: 7-Chloro-5-(2-ethyl-5-(trifluoromethyl)-2H-pyrazolo[4,3-b]pyridin-3-yl)indolin-2-one

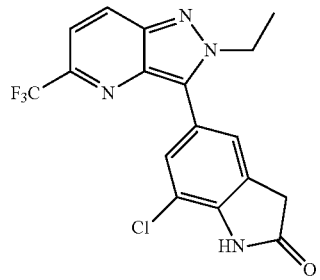 [SMILES: CCn1nc2ccc(C(F)(F)F)nc2c1-c1cc(Cl)c2c(c1)CC(=O)N2]

The title compound was prepared in a manner analogous to Example 2, substituting 2-ethyl-5-(trifluoromethyl)-2H-pyrazolo[4,3-b]pyridine (Intermediate 17) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)indolin-2-one (Intermediate 4) for 7-methyl-5-(4,4,5,5-tetramethyl-1,3,2-dioxaborolan-2-yl)indolin-2-one (Intermediate 3) in Step B. MS (ESI): mass calcd. for $C_{17}H_{12}ClF_3N_4O$, 380.1; m/z found, 381.1 [M+H]$^+$. $^1$H NMR (300 MHz, DMSO-d$_6$) δ 11.10 (s, 1H), 8.44 (d, J=9.0 Hz, 1H), 7.74 (d, J=9.0 Hz, 1H), 7.65-7.60 (m, 1H), 7.54-7.48 (m, 1H), 4.54 (q, J=7.2 Hz, 2H), 3.75 (s, 2H), 1.50 (t, J=7.2 Hz, 3H).

Example 19: 2-Ethyl-3-(7-methyl-1H-indazol-5-yl)-5-(trifluoromethyl)-2H-pyrazolo[4,3-b]pyridine

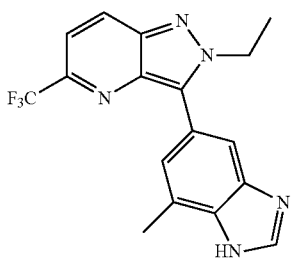 [SMILES: CCn1nc2ccc(C(F)(F)F)nc2c1-c1cc(C)c2[nH]cnc2c1]

The title compound was prepared in a manner analogous to Example 2, substituting 2-ethyl-5-(trifluoromethyl)-2H-pyrazolo[4,3-b]pyridine (Intermediate 17) for 2-methyl-5-(trifluoromethyl)-2H-pyrazolo[4,3-b]pyridine (Intermediate 16) in Step A and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{17}H_{14}F_3N_5$, 345.1; m/z found, 346.2 [M+H]$^+$. $^1$H NMR (300 MHz, DMSO-d$_6$) δ 13.47 (s, 1H), 8.43 (d, J=9.0 Hz, 1H), 8.28-8.20 (m, 1H), 7.94-7.88 (m, 1H), 7.73 (d, J=9.0 Hz, 1H), 7.46-7.38 (m, 1H), 4.55 (q, J=7.2 Hz, 2H), 2.63 (s, 3H), 1.50 (t, J=7.2 Hz, 3H).

Example 20: 3-(7-Chloro-1H-indazol-5-yl)-2-ethyl-5-(trifluoromethyl)-2H-pyrazolo[4,3-b]pyridine

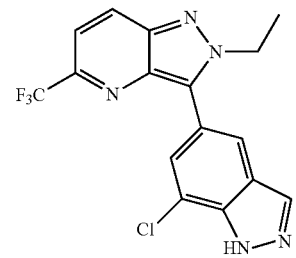 [SMILES: CCn1nc2ccc(C(F)(F)F)nc2c1-c1cc(Cl)c2[nH]ncc2c1]

The title compound was prepared in a manner analogous to Example 2, substituting 2-ethyl-5-(trifluoromethyl)-2H-pyrazolo[4,3-b]pyridine (Intermediate 17) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{16}H_{11}ClF_3N_5$, 365.1; m/z found, 366.1 [M+H]$^+$. $^1$H NMR (300 MHz, DMSO-d$_6$) δ 13.93 (br s, 1H), 8.47 (d, J=9.0 Hz, 1H), 8.40 (s, 1H), 8.12 (d, J=1.4 Hz, 1H), 7.82 (d, J=1.3 Hz, 1H), 7.75 (d, J=9.0 Hz, 1H), 4.58 (q, J=7.2 Hz, 2H), 1.51 (t, J=7.2 Hz, 3H).

Example 21: 5-(2-Isopropyl-5-(trifluoromethyl)-2H-pyrazolo[4,3-b]pyridin-3-yl)-7-methylindolin-2-one

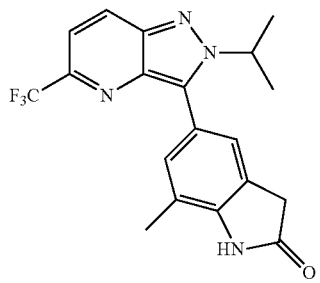

The title compound was prepared in a manner analogous to Example 2, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A. MS (ESI): mass calcd. for $C_{19}H_{17}F_3N_4O$, 374.1; m/z found, 375.1 [M+H]$^+$. $^1$H NMR (500 MHz, DMSO-d$_6$) δ 10.70 (s, 1H), 8.42 (d, J=9.0 Hz, 1H), 7.70 (d, J=9.0 Hz, 1H), 7.31-7.27 (m, 1H), 7.26-7.23 (m, 1H), 5.03-4.90 (m, 1H), 3.63 (s, 2H), 2.31 (s, 3H), 1.55 (d, J=6.5 Hz, 6H).

Example 22: 7-Chloro-5-(2-isopropyl-5-(trifluoromethyl)-2H-pyrazolo[4,3-b]pyridin-3-yl)indolin-2-one

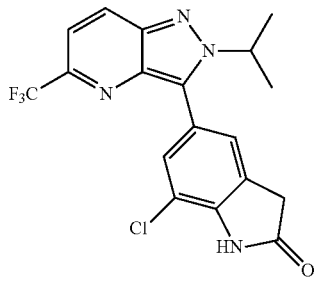

The title compound was prepared in a manner analogous to Example 2, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)indolin-2-one (Intermediate 4) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{14}ClF_3N_4O$, 394.1; m/z found, 395.1 [M+H]$^+$. $^1$H NMR (300 MHz, DMSO-d$_6$) δ 11.09 (s, 1H), 8.45 (d, J=9.0 Hz, 1H), 7.73 (d, J=9.0 Hz, 1H), 7.59-7.52 (m, 1H), 7.47-7.41 (m, 1H), 5.05-4.87 (m, 1H), 3.75 (s, 2H), 1.56 (d, J=6.5 Hz, 6H).

Example 23: 2-Isopropyl-3-(7-methyl-1H-indazol-5-yl)-5-(trifluoromethyl)-2H-pyrazolo[4,3-b]pyridine

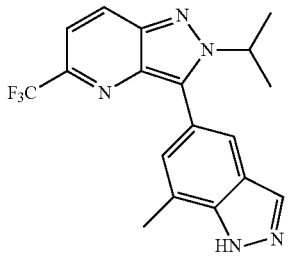 [SMILES: Cc1cc(-c2c3nc(C(F)(F)F)ccc3nn2C(C)C)cc2cn[nH]c12]

The title compound was prepared in a manner analogous to Example 2, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{16}F_3N_5$, 359.1; m/z found, 360.2 [M+H]$^+$. $^1$H NMR (300 MHz, DMSO-d$_6$) δ 13.47 (s, 1H), 8.45 (d, J=9.0 Hz, 1H), 8.24 (s, 1H), 7.92-7.81 (m, 1H), 7.72 (d, J=9.0 Hz, 1H), 7.40-7.28 (m, 1H), 5.09-4.92 (m, 1H), 2.63 (s, 3H), 1.56 (d, J=6.5 Hz, 6H).

Example 24: 3-(7-Chloro-1H-indazol-5-yl)-2-isopropyl-5-(trifluoromethyl)-2H-pyrazolo[4,3-b]pyridine

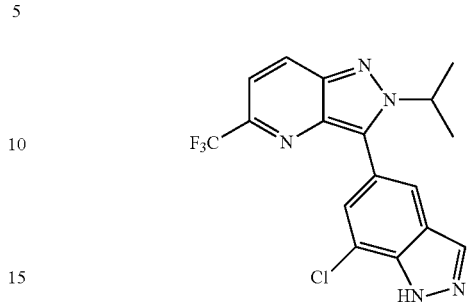

The title compound was prepared in a manner analogous to Example 2, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{17}H_{13}ClF_3N_5$, 379.1; m/z found, 380.1 [M+H]$^+$. $^1$H NMR (300 MHz, DMSO-d$_6$) δ 13.94 (br s, 1H), 8.48 (d, J=9.0 Hz, 1H), 8.40 (s, 1H), 8.06 (d, J=1.3 Hz, 1H), 7.75 (d, J=9.0 Hz, 1H), 7.75 (d, J=1.3 Hz, 1H), 5.07-4.90 (m, 1H), 1.58 (d, J=6.5 Hz, 6H).

Example 25: 5-(2-Cyclobutyl-5-(trifluoromethyl)-2H-pyrazolo[4,3-b]pyridin-3-yl)-7-methylindolin-2-one

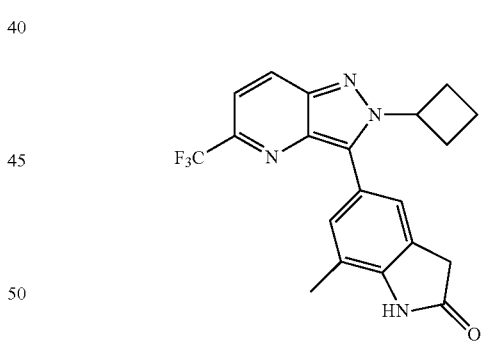

The title compound was prepared in a manner analogous to Example 2, substituting 2-cyclobutyl-5-(trifluoromethyl)-2H-pyrazolo[4,3-b]pyridine (Intermediate 12) for 2-methyl-5-(trifluoromethyl)-2H-pyrazolo[4,3-b]pyridine (Intermediate 16) in Step A. MS (ESI): mass calcd. for $C_{20}H_{17}F_3N_4O$, 386.1; m/z found, 387.2 [M+H]$^+$. $^1$H NMR (300 MHz, DMSO-d$_6$) δ 10.71 (s, 1H), 8.44 (d, J=9.0 Hz, 1H), 7.72 (d, J=9.0 Hz, 1H), 7.31-7.25 (m, 1H), 7.25-7.21 (m, 1H), 5.35-5.19 (m, 1H), 3.63 (s, 2H), 2.90-2.70 (m, 2H), 2.49-2.38 (m, 2H), 2.31 (s, 3H), 1.99-1.80 (m, 2H).

Example 26: 7-Chloro-5-(2-cyclobutyl-5-(trifluoromethyl)-2H-pyrazolo[4,3-b]pyridin-3-yl)indolin-2-one

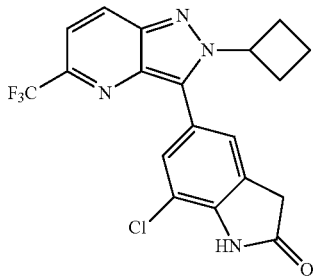 [SMILES: O=C1Cc2cc(-c3c4nc(C(F)(F)F)ccc4nn3C3CCC3)cc(Cl)c2N1]

The title compound was prepared in a manner analogous to Example 2, substituting substituting 2-cyclobutyl-5-(trifluoromethyl)-2H-pyrazolo[4,3-b]pyridine (Intermediate 12) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)indolin-2-one (Intermediate 4) for 7-methyl-5-(4,4,5,5-tetramethyl-1,3,2-dioxaborolan-2-yl)indolin-2-one (Intermediate 3) in Step B. MS (ESI): mass calcd. for $C_{19}H_{14}ClF_3N_4O$, 406.1; m/z found, 407.1 [M+H]$^+$. $^1$H NMR (300 MHz, DMSO-d$_6$) δ 11.09 (s, 1H), 8.47 (d, J=9.0 Hz, 1H), 7.74 (d, J=9.0 Hz, 1H), 7.56-7.51 (m, 1H), 7.45-7.40 (m, 1H), 5.36-5.22 (m, 1H), 3.75 (s, 2H), 2.87-2.69 (m, 2H), 2.52-2.37 (m, 2H), 2.00-1.80 (m, 2H).

Example 27: 2-Cyclobutyl-3-(7-methyl-1H-indazol-5-yl)-5-(trifluoromethyl)-2H-pyrazolo[4,3-b]pyridine

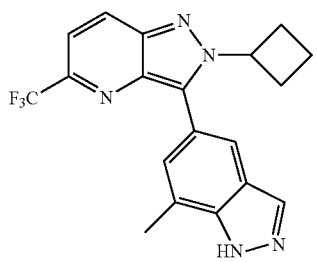

The title compound was prepared in a manner analogous to Example 2, substituting substituting 2-cyclobutyl-5-(trifluoromethyl)-2H-pyrazolo[4,3-b]pyridine (Intermediate 12) for 2-methyl-5-(trifluoromethyl)-2H-pyrazolo[4,3-b]pyridine (Intermediate 16) in Step A and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{19}H_{16}F_3N_5$, 371.1; m/z found, 372.1 [M+H]$^+$. $^1$H NMR (500 MHz, DMSO-d$_6$) δ 13.45 (br s, 1H), 8.47 (d, J=9.0 Hz, 1H), 8.25 (s, 1H), 7.85 (s, 1H), 7.73 (d, J=9.0 Hz, 1H), 7.34 (s, 1H), 5.36-5.26 (m, 1H), 2.88-2.76 (m, 2H), 2.63 (s, 3H), 2.48-2.40 (m, 2H), 1.96-1.80 (m, 2H).

Example 28: 3-(7-Chloro-1H-indazol-5-yl)-2-cyclobutyl-5-(trifluoromethyl)-2H-pyrazolo[4,3-b]pyridine

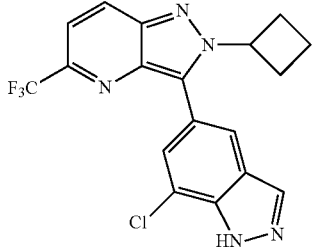

The title compound was prepared in a manner analogous to Example 2, substituting substituting 2-cyclobutyl-5-(trifluoromethyl)-2H-pyrazolo[4,3-b]pyridine (Intermediate 12) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{13}ClF_3N_5$, 391.1; m/z found, 392.1 [M+H]$^+$. $^1$H NMR (300 MHz, DMSO-d$_6$) δ 13.94 (br s, 1H), 8.50 (d, J=9.0 Hz, 1H), 8.41 (s, 1H), 8.04 (d, J=1.3 Hz, 1H), 7.76 (d, J=9.1 Hz, 1H), 7.73 (d, J=1.3 Hz, 1H), 5.42-5.28 (m, 1H), 2.89-2.73 (m, 2H), 2.50-2.38 (m, 2H), 1.98-1.81 (m, 2H).

Example 29: 7-Chloro-5-(2-(difluoromethyl)-5-(trifluoromethyl)-2H-pyrazolo[4,3-b]pyridin-3-yl)indolin-2-one

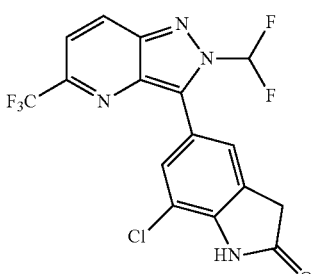

The title compound was prepared in a manner analogous to Example 3, substituting 7-chloro-5-(4,4,5,5-tetramethyl-1,3,2-dioxaborolan-2-yl)indolin-2-one (Intermediate 4) for 7-methyl-5-(4,4,5,5-tetramethyl-1,3,2-dioxaborolan-2-yl)indolin-2-one (Intermediate 3) in Step B. MS (ESI): mass calcd. for $C_{16}H_8ClF_5N_4O$, 402.0; m/z found, 403.0 [M+H]$^+$. $^1$H NMR (300 MHz, DMSO-d$_6$) δ 11.18 (s, 1H), 8.60 (d, J=9.1 Hz, 1H), 8.20 (t, J=56.8 Hz, 1H), 7.89 (d, J=9.2 Hz, 1H), 7.65-7.60 (m, 1H), 7.53-7.47 (m, 1H), 3.76 (s, 2H).

Example 30: 2-(Difluoromethyl)-3-(7-methyl-1H-indazol-5-yl)-5-(trifluoromethyl)-2H-pyrazolo[4,3-b]pyridine

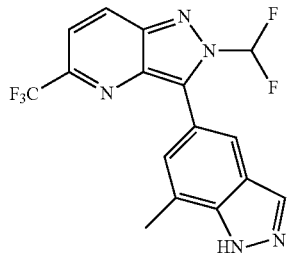 [SMILES: Cc1cc(-c2c3nc(C(F)(F)F)ccc3nn2C(F)F)cc2cn[nH]c12]

The title compound was prepared in a manner analogous to Example 3, substituting 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{16}H_{10}F_5N_5$, 367.3; m/z found, 368.1 [M+H]$^+$. $^1$H NMR (500 MHz, DMSO-d$_6$) δ 13.54 (s, 1H), 8.60 (d, J=9.2 Hz, 1H), 8.29 (s, 1H), 8.12 (t, J=56.8 Hz, 1H), 7.98-7.93 (m, 1H), 7.88 (d, J=9.2 Hz, 1H), 7.46-7.40 (m, 1H), 2.63 (s, 3H).

Example 31: 3-(7-Chloro-1H-indazol-5-yl)-2-(difluoromethyl)-5-(trifluoromethyl)-2H-pyrazolo[4,3-b]pyridine

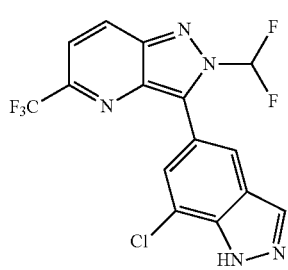 [SMILES: FC(F)n1nc2ccc(C(F)(F)F)nc2c1-c1cc(Cl)c2[nH]ncc2c1]

The title compound was prepared in a manner analogous to Example 3, substituting 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{15}H_7ClF_5N_5$, 387.0; m/z found, 388.0 [M+H]$^+$. $^1$H NMR (300 MHz, DMSO-d$_6$) δ 14.02 (s, 1H), 8.63 (d, J=9.2 Hz, 1H), 8.45 (s, 1H), 8.23 (t, J=56.8 Hz, 1H), 8.12 (d, J=0.9 Hz, 1H), 7.90 (d, J=9.2 Hz, 1H), 7.81 (d, J=0.8 Hz, 1H).

Example 32: 6-(2-Isopropyl-5-(trifluoromethyl)-2H-pyrazolo[4,3-b]pyridin-3-yl)benzo[d]thiazol-2(3H)-one

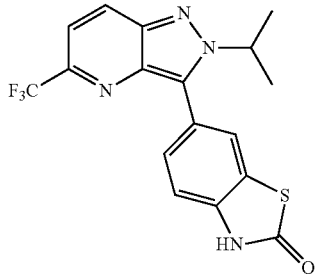 [SMILES: CC(C)n1nc2ccc(C(F)(F)F)nc2c1-c1ccc2[nH]c(=O)sc2c1]

The title compound may be prepared in a manner analogous to Example 2, substituting 2-isopropyl-5-(trifluoromethyl)-2H-pyrazolo[4,3-b]pyridine (Intermediate 11) for 2-methyl-5-(trifluoromethyl)-2H-pyrazolo[4,3-b]pyridine (Intermediate 16) in Step A and 6-(4,4,5,5-tetramethyl-1,3,2-dioxaborolan-2-yl)benzo[d]thiazol-2(3H)-one (Intermediate 19) for 7-methyl-5-(4,4,5,5-tetramethyl-1,3,2-dioxaborolan-2-yl)indolin-2-one (Intermediate 3) in Step B

Example 33: 3-(7-Chloro-1H-indazol-5-yl)-5-(difluoromethyl)-2-isopropyl-2H-pyrazolo[4,3-b]pyridine

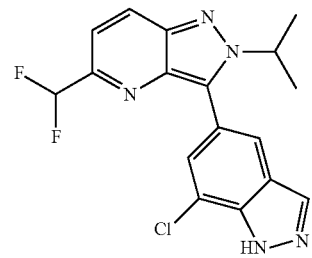 [SMILES: CC(C)n1nc2ccc(C(F)F)nc2c1-c1cc(Cl)c2[nH]ncc2c1]

The title compound may be prepared according to the methods described in SCHEME 5 and SCHEME 6, using 2-iodopropane and 7-chloro-5-(4,4,5,5-tetramethyl-1,3,2-dioxaborolan-2-yl)-1H-indazole (Intermediate 6).

Example 34: 5-(Difluoromethyl)-2-isopropyl-3-(7-methyl-1H-indazol-5-yl)-2H-pyrazolo[4,3-b]pyridine

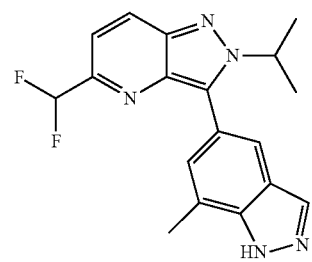

The title compound was prepared in a manner analogous to Example 2, substituting 3-bromo-5-(difluoromethyl)-2- isopropyl-2H-pyrazolo[4,3-b]pyridine (Intermediate 21) for 3-bromo-2-methyl-5-(trifluoromethyl)-2H-pyrazolo[4,3-b]pyridine and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{17}F_2N_5$, 341.2; m/z found, 342.2 [M+H]$^+$. $^1$H NMR (500 MHz, DMSO-$d_6$): 13.43 (s, 1H), 8.36 (d, J=9.0 Hz, 1H), 8.22 (d, J=1.4 Hz, 1H), 7.86-7.83 (m, 1H), 7.58 (d, J=9.0 Hz, 1H), 7.36-7.32 (m, 1H), 6.92 (t, J=54.9 Hz, 1H), 5.02-4.92 (m, 1H), 2.63 (s, 3H), 1.56 (d, J=6.5 Hz, 6H).

Example 35: 5-(5-(Difluoromethyl)-2-isopropyl-2H-pyrazolo[4,3-b]pyridin-3-yl)-7-methylindolin-2-one

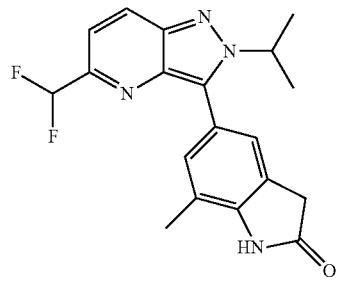

The title compound may be prepared according to the methods described in SCHEME 5 and SCHEME 6, using 2-iodopropane and 7-methyl-5-(4,4,5,5-tetramethyl-1,3,2-dioxaborolan-2-yl)-indolin-2-one (Intermediate 3).

Example 36: 7-Chloro-5-(5-(difluoromethyl)-2-isopropyl-2H-pyrazolo[4,3-b]pyridin-3-yl)indolin-2-one

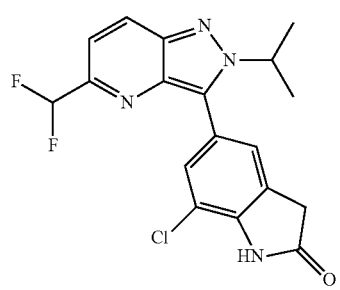

The title compound was prepared in a manner analogous to Example 2, substituting 3-bromo-5-(difluoromethyl)-2-isopropyl-2H-pyrazolo[4,3-b]pyridine (Intermediate 21) for 3-bromo-2-methyl-5-(trifluoromethyl)-2H-pyrazolo[4,3-b]pyridine and 7-chloro-5-(4,4,5,5-tetramethyl-1,3,2-dioxaborolan-2-yl)indolin-2-one (Intermediate 4)) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{15}ClF_2N_4O$, 376.1; m/z found, 376.9 [M+H]$^+$. $^1$H NMR (500 MHz, DMSO-$d_6$): 11.06 (s, 1H), 8.35 (d, J=9.0 Hz, 1H), 7.58 (d, J=9.0 Hz, 1H), 7.55-7.51 (m, 1H), 7.44-7.41 (m, 1H), 6.95 (t, J=54.9 Hz, 1H), 4.97-4.88 (m, 1H), 3.74 (s, 2H), 1.55 (d, J=6.5 Hz, 6H).

Example 37: 6-(5-(Difluoromethyl)-2-isopropyl-2H-pyrazolo[4,3-b]pyridin-3-yl)benzo[d]thiazol-2(3H)-one

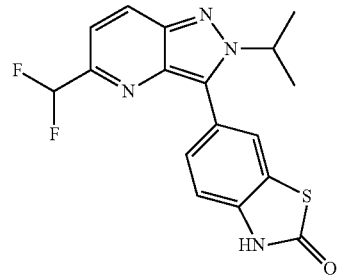 [SMILES: Cc1cc(-c2c3nc(C(F)F)ccc3nn2C(C)C)cc2c1NC(=O)C2]

The title compound may be prepared according to the methods described in SCHEME 5 and SCHEME 6, using 2-iodopropane and 6-(4,4,5,5-tetramethyl-1,3,2-dioxaborolan-2-yl)benzo[d]thiazol-2(3H)-one (Intermediate 19).

Example 38: 7-(Difluoromethyl)-2-isopropyl-3-(7-methyl-1H-indazol-5-yl)pyrazolo[4,3-b]pyridine

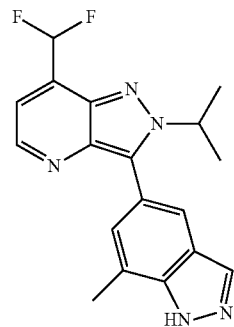 [SMILES: Cc1cc(-c2c3nccc(C(F)F)c3nn2C(C)C)cc2cn[nH]c12]

The title compound was prepared in a manner analogous to Example 2, substituting 3-bromo-7-(difluoromethyl)-2-isopropyl-2H-pyrazolo[4,3-b]pyridine (Intermediate 22) for 3-bromo-2-methyl-5-(trifluoromethyl)-2H-pyrazolo[4,3-b]pyridine and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{18}H_{17}F_2N_5$, 341.2; m/z found, 342.2 [M+H]$^+$. $^1$H NMR (500 MHz, CDCl$_3$): 11.13 (br s, 1H), 8.73 (d, J=4.3 Hz, 1H), 8.11 (s, 1H), 7.71-7.68 (m, 1H), 7.51-7.48 (m, 1H), 7.34 (t, J=55.0 Hz, 1H), 7.21-7.18 (m, 1H), 5.03-4.93 (m, 1H), 2.50 (s, 3H), 1.65 (d, J=6.6 Hz, 6H).

Example 39: 3-(7-Chloro-1H-indazol-5-yl)-2-isopropyl-pyrazolo[4,3-b]pyridine

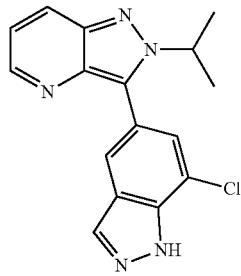 [SMILES: CC(C)n1nc2cccnc2c1-c1cc(Cl)c2[nH]ncc2c1]

The title compound was prepared in a manner analogous to Example 2, substituting 2-isopropylpyrazolo[4,3-b]pyridine (Intermediate 20) for 2-methyl-5-(trifluoromethyl)-2H-pyrazolo[4,3-b]pyridine (Intermediate 16) in Step A and 7-chloro-5-(4,4,5,5-tetramethyl-1,3,2-dioxaborolan-2-yl)-1H-indazole (Intermediate 6) for 7-methyl-5-(4,4,5,5-tetramethyl-1,3,2-dioxaborolan-2-yl)indolin-2-one (Intermediate 3) in Step B. MS (ESI): mass calcd. for $C_{16}H_{14}ClN_5$, 311.1; m/z found, 312.1 [M+H]$^+$. $^1$H NMR (500 MHz, DMSO-$d_6$) δ 13.87 (br s, 1H), 8.51 (dd, J=4.1, 1.5 Hz, 1H), 8.39-8.33 (m, 1H), 8.16 (dd, J=8.8, 1.4 Hz, 1H), 8.03 (d, J=1.3 Hz, 1H), 7.75-7.71 (m, 1H), 7.32 (dd, J=8.7, 4.0 Hz, 1H), 5.05-4.95 (m, 1H), 1.57 (d, J=6.5 Hz, 6H).

Example 40: 5,7-Bis(difluoromethyl)-2-isopropyl-3-(7-methyl-1H-indazol-5-yl)pyrazolo[4,3-b]pyridine

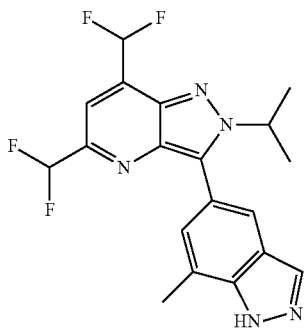 [SMILES: Cc1cc(-c2c3nc(C(F)F)cc(C(F)F)c3nn2C(C)C)cc2cn[nH]c12]

The title compound was prepared in a manner analogous to Example 2, substituting 3-bromo-5,7-bis(difluoromethyl)-2-isopropyl-2H-pyrazolo[4,3-b]pyridine (Intermediate 23) for 3-bromo-2-methyl-5-(trifluoromethyl)-2H-pyrazolo[4,3-b]pyridine and 7-methyl-5-(4,4,5,5-tetramethyl-1,3,2-dioxaborolan-2-yl)-1H-indazole (Intermediate 5) for 7-methyl-5-(4,4,5,5-tetramethyl-1,3,2-dioxaborolan-2-yl)indolin-2-one (Intermediate 3) in Step B. MS (ESI): mass calcd. for $C_{19}H_{17}F_4N_5$, 391.1; m/z found, 392.2 [M+H]$^+$. 1H NMR (500 MHz, DMSO-$d_6$): 13.47 (s, 1H), 8.25 (s, 1H), 7.91-7.86 (m, 1H), 7.78-7.74 (m, 1H), 7.58 (t, J=54.0 Hz, 1H), 7.38-7.34 (m, 1H), 7.03 (t, J=54.6 Hz, 1H), 5.05-4.96 (m, 1H), 2.64 (s, 3H), 1.58 (d, J=6.6 Hz, 6H).

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904). An in vitro assay was used to determine the potency of test compounds as inhibitors of the glutamate response of the channel formed by GluA1o-γ8. To ensure a 1:1 stoichiometry of GluA1o and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): 633-640), the C-terminus of the cDNA for GRIA1o was fused to the N-terminus of the cDNA for γ8. The linker sequence was QQQQQQQQQQE-FAT. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay.

Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$, 1 mM $MgCl_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 μM glutamate was monitored using a Molecular Devices FLIPR Tetra. The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." *Neuropharmacology* 42(2): 143-153). The responses to glutamate as functions of the test compound concentrations were fitted to a four-parameter logistic function. The fitted parameter corresponding to the midpoint was taken to be the potency of inhibition of the compound. The data in Table 3 below illustrates the observed potentcy for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 3

| Ex # | Compound Name | $pIC_{50}$ |
|---|---|---|
| 1 | 5-(2-Methyl-5-(trifluoromethyl)-2H-pyrazolo[4,3-b]pyridin-3-yl)-1,3-dihydro-2H-benzo[d]imidazol-2-one; | 6.5 |
| 2 | 7-Methyl-5-(2-methyl-5-(trifluoromethyl)-2H-pyrazolo[4,3-b]pyridin-3-yl)indolin-2-one; | 7.9 |

TABLE 3-continued

| Ex # | Compound Name | pIC$_{50}$ |
|---|---|---|
| 3 | 5-[2-(Difluoromethyl)-5-(trifluoromethyl)pyrazolo[4,3-b]pyridin-3-yl]-7-methyl-indolin-2-one; | 9.0 |
| 4 | 5-(2-Ethyl-5-(trifluoromethyl)-2H-pyrazolo[4,3-b]pyridin-3-yl)-1,3-dihydro-2H-benzo[d]imidazol-2-one; | 7.0 |
| 5 | 5-(2-Isopropyl-5-(trifluoromethyl)-2H-pyrazolo[4,3-b]pyridin-3-yl)-1,3-dihydro-2H-benzo[d]imidazol-2-one; | 7.6 |
| 6 | 5-(2-(Cyclobutylmethyl)-5-(trifluoromethyl)-2H-pyrazolo[4,3-b]pyridin-3-yl)-1,3-dihydro-2H-benzo[d]imidazol-2-one; | 6.9 |
| 7 | 5-(2-Cyclopentyl-5-(trifluoromethyl)-2H-pyrazolo[4,3-b]pyridin-3-yl)-1,3-dihydro-2H-benzo[d]imidazol-2-one; | 7.8 |
| 8 | 2-Cyclopentyl-3-(7-methyl-1H-indazol-5-yl)-5-(trifluoromethyl)-2H-pyrazolo[4,3-b]pyridine; | 9.9 |
| 9 | 5-(2-Phenyl-5-(trifluoromethyl)-2H-pyrazolo[4,3-b]pyridin-3-yl)-1,3-dihydro-2H-benzo[d]imidazol-2-one; | 8.8 |
| 10 | 5-(2-Phenyl-5-(trifluoromethyl)-2H-pyrazolo[4,3-b]pyridin-3-yl)indolin-2-one; | 8.2 |
| 11 | 3-(1H-Indazol-5-yl)-2-phenyl-5-(trifluoromethyl)-pyrazolo[4,3-b]pyridine; | 8.5 |
| 12 | 2-Cyclobutyl-3-(1H-indazol-5-yl)-5-(trifluoromethyl)-2H-pyrazolo[4,3-b]pyridine; | 9.2 |
| 13 | 3-(1H-Indazol-5-yl)-2-(2-methoxyethyl)-5-(trifluoromethyl)-2H-pyrazolo[4,3-b]pyridine; | 6.1 |
| 14 | 3-(1H-Indazol-5-yl)-2-(pyridin-2-yl)-5-(trifluoromethyl)-2H-pyrazolo[4,3-b]pyridine; | 6.9 |
| 15 | 2-Methyl-3-(7-methyl-1H-indazol-5-yl)-5-(trifluoromethyl)-2H-pyrazolo[4,3-b]pyridine; | 9.0 |
| 16 | 3-(7-Chloro-1H-indazol-5-yl)-2-methyl-5-(trifluoromethyl)-2H-pyrazolo[4,3-b]pyridine; | 9.5 |
| 17 | 5-(2-Ethyl-5-(trifluoromethyl)-2H-pyrazolo[4,3-b]pyridin-3-yl)-7-methylindolin-2-one; | 8.3 |
| 18 | 7-Chloro-5-(2-ethyl-5-(trifluoromethyl)-2H-pyrazolo[4,3-b]pyridin-3-yl)indolin-2-one; | 8.6 |
| 19 | 2-Ethyl-3-(7-methyl-1H-indazol-5-yl)-5-(trifluoromethyl)-2H-pyrazolo[4,3-b]pyridine; | 9.1 |
| 20 | 3-(7-Chloro-1H-indazol-5-yl)-2-ethyl-5-(trifluoromethyl)-2H-pyrazolo[4,3-b]pyridine; | 9.4 |
| 21 | 5-(2-Isopropyl-5-(trifluoromethyl)-2H-pyrazolo[4,3-b]pyridin-3-yl)-7-methylindolin-2-one; | 9.4 |
| 22 | 7-Chloro-5-(2-isopropyl-5-(trifluoromethyl)-2H-pyrazolo[4,3-b]pyridin-3-yl)indolin-2-one; | 9.6 |
| 23 | 2-Isopropyl-3-(7-methyl-1H-indazol-5-yl)-5-(trifluoromethyl)-2H-pyrazolo[4,3-b]pyridine; | 9.6 |
| 24 | 3-(7-Chloro-1H-indazol-5-yl)-2-isopropyl-5-(trifluoromethyl)-2H-pyrazolo[4,3-b]pyridine; | 10.2 |
| 25 | 5-(2-Cyclobutyl-5-(trifluoromethyl)-2H-pyrazolo[4,3-b]pyridin-3-yl)-7-methylindolin-2-one; | 10.3 |
| 26 | 7-Chloro-5-(2-cyclobutyl-5-(trifluoromethyl)-2H-pyrazolo[4,3-b]pyridin-3-yl)indolin-2-one; | 10.5 |
| 27 | 2-Cyclobutyl-3-(7-methyl-1H-indazol-5-yl)-5-(trifluoromethyl)-2H-pyrazolo[4,3-b]pyridine; | 10.7 |
| 28 | 3-(7-Chloro-1H-indazol-5-yl)-2-cyclobutyl-5-(trifluoromethyl)-2H-pyrazolo[4,3-b]pyridine; | 10.7 |
| 29 | 7-Chloro-5-(2-(difluoromethyl)-5-(trifluoromethyl)-2H-pyrazolo[4,3-b]pyridin-3-yl)indolin-2-one; | 8.6 |
| 30 | 2-(Difluoromethyl)-3-(7-methyl-1H-indazol-5-yl)-5-(trifluoromethyl)-2H-pyrazolo[4,3-b]pyridine; | 9.2 |
| 31 | 3-(7-Chloro-1H-indazol-5-yl)-2-(difluoromethyl)-5-(trifluoromethyl)-2H-pyrazolo[4,3-b]pyridine; | 9.2 |
| 34 | 5-(Difluoromethyl)-2-isopropyl-3-(7-methyl-1H-indazol-5-yl)-2H-pyrazolo[4,3-b]pyridine; | 10.0 |
| 36 | 7-Chloro-5-(5-(difluoromethyl)-2-isopropyl-2H-pyrazolo[4,3-b]pyridin-3-yl)indolin-2-one; | 9.4 |
| 38 | 7-(Difluoromethyl)-2-isopropyl-3-(7-methyl-1H-indazol-5-yl)pyrazolo[4,3-b]pyridine; | 6.9 |
| 39 | 3-(7-Chloro-1H-indazol-5-yl)-2-isopropyl-pyrazolo[4,3-b]pyridine; and | 7.2 |
| 40 | 5,7-Bis(difluoromethyl)-2-isopropyl-3-(7-methyl-1H-indazol-5-yl)pyrazolo[4,3-b]pyridine. | 9.8 |

Electrophysiology Assay

The effects of selected compounds upon endogenous gamma8-containing AMPA receptor currents are evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003). Hippocampi are dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice are asphyxiated with $CO_2$ then decapitated. The brain is rapidly removed, then placed into ice-cold HABG medium. The recipe for HABG medium is: HibernateA supplemented with 2% B27 and 0.5 mM Glutamax (all reagents from Life Technologies). Hippocampi are micro-dissected from the brains, then washed with HABG without calcium (Hibernate A minus Calcium, BrainBits; 2% B27, Life Technologies; 0.5 mM glutamax, Life Technologies).

The hippocampi are then transferred to HABG without calcium, supplemented with 2 mg/mL papain (Worthington Biochemical). They are incubated at 30° C. on a roller for 40 min, then gently triturated with a fire-polished glass pipette. The supernatant containing dissociated neurons is collected, then centrifuged for 2 min at 200 g. The cell pellet is collected, and then resuspended in 8 mL of HABG. Live cells are counted, then plated onto 12 mm glass coverslips in 2 mL of HABG in 24-well plates at a density of 50-100 cells per coverslip. These cells are maintained at rt until use. Whole-cell electrophysiology is performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290mOs. The extracellular buffer was 135 mM NaCl, 4 mM KCl, 2 mM $CaCl_2$, 1 mM $MgCl_2$, 5 mM glucose, 10 mM HEPES, pH 7.4, 300 mOs. The open-tip resistances of the micropipettes using these solutions are 2-4 MΩ. Whole-cell recordings of neuron cell bodies are performed in voltage-clamp mode using an Axon Axopatch 200B amplifier. Whole-cell current is measured holding the interior of the cell at −60 mV, using a 5 kHz lowpass filter. The cells are continuously perfused through 7 mm square glass barrels using a solenoid-controlled solution switching device (Warner Instruments, PF-77B). The peak current in response to a 500 ms exposure to 10 mM glutamate every 5 seconds is measured, before and after exposure to test compound.

For analysis, the mean peak current of 5 traces in the presence of test compound is divided by the mean peak current of 5 traces prior to the addition of test compound. Compounds are tested at concentrations at least ten times higher than their estimated potency in the calcium flux assay, in order to ensure near-saturating occupancy of the receptor.

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula (I):

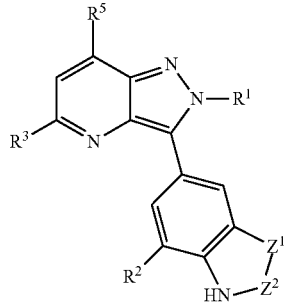
(I)

wherein
- $R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl;
- $R^2$ is selected from the group consisting of: H, halo, and $CH_3$;
- $R^3$ is $C_{1-6}$haloalkyl;

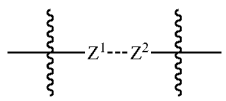

is selected from the group consisting of: —CH=N—, —CH$_2$—C(=O)—, —S—C(=O)—, and —NH—C(=O)—; and
- $R^5$ is H or $CHF_2$; and pharmaceutically acceptable salts, N-oxides, or solvates thereof.

2. The compound of claim 1, wherein $R^1$ is $C_{1-6}$alkyl, $C_{1-6}$haloalkyl, $CH_2CH_2OCH_3$, $CH_2$cyclobutyl, cyclobutyl, cyclopentyl, phenyl, or pyridin-2-yl.

3. The compound of claim 1, wherein $R^2$ is H, Cl or $CH_3$.

4. The compound of claim 1, wherein $R^3$ is $CF_3$.

5. The compound of claim 1, wherein $R^3$ is $CF_2H$.

6. The compound of claim 1, wherein

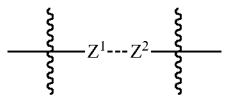

is —CH=N—.

7. The compound of claim 1, wherein

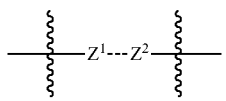

is —CH$_2$—C(=O)—.

8. The compound of claim 1, wherein

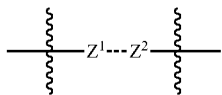

is —NH—C(=O)—.

9. The compound of claim 1, wherein

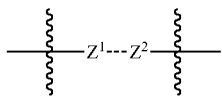

is —S—C(=O)—.

10. The compound of claim 1, wherein $R^5$ is H.

11. The compound of claim 1, wherein $R^5$ is $CHF_2$.

12. The compound of claim 1, and pharmaceutically acceptable salts, solvates, or N-oxides thereof, having the structure of Formula (IA):

(IA)

wherein
- $R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl; and
- $R^4$ is selected from the group consisting of:

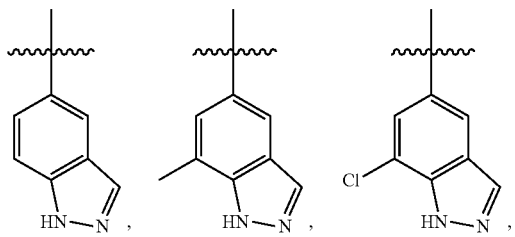

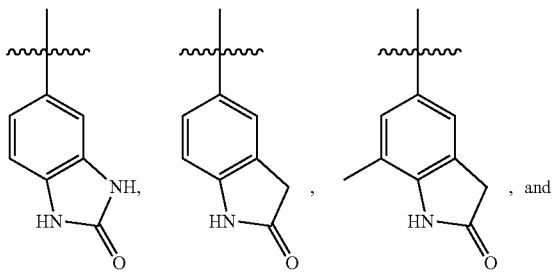

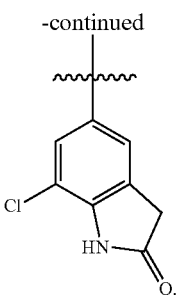

13. A compound selected from the group consisting of:
5-(2-Methyl-5-(trifluoromethyl)-2H-pyrazolo[4,3-b]pyridin-3-yl)-1,3-dihydro-2H-benzo[d]imidazol-2-one;
7-Methyl-5-(2-methyl-5-(trifluoromethyl)-2H-pyrazolo[4,3-b]pyridin-3-yl)indolin-2-one;
5-[2-(Difluoromethyl)-5-(trifluoromethyl)pyrazolo[4,3-b]pyridin-3-yl]-7-methyl-indolin-2-one;
5-(2-Ethyl-5-(trifluoromethyl)-2H-pyrazolo[4,3-b]pyridin-3-yl)-1,3-dihydro-2H-benzo[d]imidazol-2-one;
5-(2-Isopropyl-5-(trifluoromethyl)-2H-pyrazolo[4,3-b]pyridin-3-yl)-1,3-dihydro-2H-benzo[d]imidazol-2-one;
5-(2-(Cyclobutylmethyl)-5-(trifluoromethyl)-2H-pyrazolo[4,3-b]pyridin-3-yl)-1,3-dihydro-2H-benzo[d]imidazol-2-one;
5-(2-Cyclopentyl-5-(trifluoromethyl)-2H-pyrazolo[4,3-b]pyridin-3-yl)-1,3-dihydro-2H-benzo[d]imidazol-2-one;
2-Cyclopentyl-3-(7-methyl-1H-indazol-5-yl)-5-(trifluoromethyl)-2H-pyrazolo[4,3-b]pyridine;
5-(2-Phenyl-5-(trifluoromethyl)-2H-pyrazolo[4,3-b]pyridin-3-yl)-1,3-dihydro-2H-benzo[d]imidazol-2-one;
5-(2-Phenyl-5-(trifluoromethyl)-2H-pyrazolo[4,3-b]pyridin-3-yl)indolin-2-one;
3-(1H-Indazol-5-yl)-2-phenyl-5-(trifluoromethyl)-2H-pyrazolo[4,3-b]pyridine;
2-Cyclobutyl-3-(1H-indazol-5-yl)-5-(trifluoromethyl)-2H-pyrazolo[4,3-b]pyridine;
3-(1H-Indazol-5-yl)-2-(2-methoxyethyl)-5-(trifluoromethyl)-2H-pyrazolo[4,3-b]pyridine;
3-(1H-Indazol-5-yl)-2-(pyridin-2-yl)-5-(trifluoromethyl)-2H-pyrazolo[4,3-b]pyridine;
2-Methyl-3-(7-methyl-1H-indazol-5-yl)-5-(trifluoromethyl)-2H-pyrazolo[4,3-b]pyridine;
3-(7-Chloro-1H-indazol-5-yl)-2-methyl-5-(trifluoromethyl)-2H-pyrazolo[4,3-b]pyridine;
5-(2-Ethyl-5-(trifluoromethyl)-2H-pyrazolo[4,3-b]pyridin-3-yl)-7-methylindolin-2-one;
7-Chloro-5-(2-ethyl-5-(trifluoromethyl)-2H-pyrazolo[4,3-b]pyridin-3-yl)indolin-2-one;
2-Ethyl-3-(7-methyl-1H-indazol-5-yl)-5-(trifluoromethyl)-2H-pyrazolo[4,3-b]pyridine;
3-(7-Chloro-1H-indazol-5-yl)-2-ethyl-5-(trifluoromethyl)-2H-pyrazolo[4,3-b]pyridine;
5-(2-Isopropyl-5-(trifluoromethyl)-2H-pyrazolo[4,3-b]pyridin-3-yl)-7-methylindolin-2-one;
7-Chloro-5-(2-isopropyl-5-(trifluoromethyl)-2H-pyrazolo[4,3-b]pyridin-3-yl)indolin-2-one;
2-Isopropyl-3-(7-methyl-1H-indazol-5-yl)-5-(trifluoromethyl)-2H-pyrazolo[4,3-b]pyridine;
3-(7-Chloro-1H-indazol-5-yl)-2-isopropyl-5-(trifluoromethyl)-2H-pyrazolo[4,3-b]pyridine;
5-(2-Cyclobutyl-5-(trifluoromethyl)-2H-pyrazolo[4,3-b]pyridin-3-yl)-7-methylindolin-2-one;
7-Chloro-5-(2-cyclobutyl-5-(trifluoromethyl)-2H-pyrazolo[4,3-b]pyridin-3-yl)indolin-2-one;
2-Cyclobutyl-3-(7-methyl-1H-indazol-5-yl)-5-(trifluoromethyl)-2H-pyrazolo[4,3-b]pyridine;
3-(7-Chloro-1H-indazol-5-yl)-2-cyclobutyl-5-(trifluoromethyl)-2H-pyrazolo[4,3-b]pyridine;
7-Chloro-5-(2-(difluoromethyl)-5-(trifluoromethyl)-2H-pyrazolo[4,3-b]pyridin-3-yl)indolin-2-one;
2-(Difluoromethyl)-3-(7-methyl-1H-indazol-5-yl)-5-(trifluoromethyl)-2H-pyrazolo[4,3-b]pyridine;
3-(7-Chloro-1H-indazol-5-yl)-2-(difluoromethyl)-5-(trifluoromethyl)-2H-pyrazolo[4,3-b]pyridine;
5-(Difluoromethyl)-2-isopropyl-3-(7-methyl-1H-indazol-5-yl)-2H-pyrazolo[4,3-b]pyridine;
7-Chloro-5-(5-(difluoromethyl)-2-isopropyl-2H-pyrazolo[4,3-b]pyridin-3-yl)indolin-2-one;
7-(Difluoromethyl)-2-isopropyl-3-(7-methyl-1H-indazol-5-yl)pyrazolo[4,3-b]pyridine;
3-(7-Chloro-1H-indazol-5-yl)-2-isopropyl-pyrazolo[4,3-b]pyridine; and
5,7-Bis(difluoromethyl)-2-isopropyl-3-(7-methyl-1H-indazol-5-yl)pyrazolo[4,3-b]pyridine; and
pharmaceutically acceptable salts, N-oxides or solvates thereof.

14. A compound selected from the group consisting of:
6-(2-Isopropyl-5-(trifluoromethyl)-2H-pyrazolo[4,3-b]pyridin-3-yl)benzo[d]thiazol-2(3H)-one;
3-(7-Chloro-1H-indazol-5-yl)-5-(difluoromethyl)-2-isopropyl-2H-pyrazolo[4,3-b]pyridine;
5-(5-(Difluoromethyl)-2-isopropyl-2H-pyrazolo[4,3-b]pyridin-3-yl)-7-methylindolin-2-one; and
6-(5-(Difluoromethyl)-2-isopropyl-2H-pyrazolo[4,3-b]pyridin-3-yl)benzo[d]thiazol-2(3H)-one; and
pharmaceutically acceptable salts, N-oxides or solvates thereof.

15. A pharmaceutical composition comprising:
(A) an effective amount of at least one compound of Formula (I):

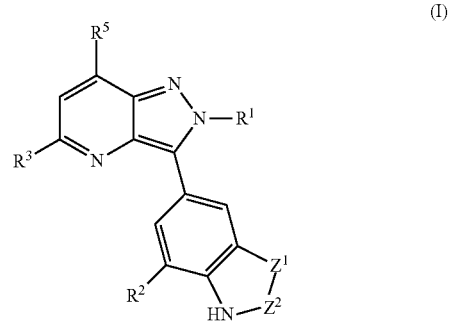

wherein
$R^1$ is selected from the group consisting of: $C_{1-6}$alkyl, $C_{1-6}$haloalkyl, $CH_2CH_2OCH_3$, $C_{3-8}$cycloalkyl, $CH_2$—$C_{3-8}$cycloalkyl, phenyl and pyridyl;
$R^2$ is selected from the group consisting of: H, halo, and $CH_3$;
$R^3$ is $C_{1-6}$haloalkyl;

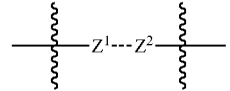

is selected from the group consisting of: —CH=N—, —CH$_2$—C(=O)—, —S—C(=O)—, and —NH—C(=O)—; and R$^5$ is H or CHF$_2$; and pharmaceutically acceptable salts, N-oxides or solvates of compounds of Formula (I); and (B) at least one pharmaceutically acceptable excipient.

16. A pharmaceutical composition comprising an effective amount of at least one compound of claim 13 and at least one pharmaceutically acceptable excipient.

* * * * *